(12) United States Patent
Lipkens et al.

(10) Patent No.: US 10,814,253 B2
(45) Date of Patent: *Oct. 27, 2020

(54) LARGE SCALE ACOUSTIC SEPARATION DEVICE

(71) Applicant: FloDesign Sonics, Inc., Wilbraham, MA (US)

(72) Inventors: Bart Lipkens, Bloomfield, CT (US); Walter M. Presz, Jr., Wilbraham, MA (US); Jeffrey King, Coventry, CT (US); Jason Barnes, Westfield, MA (US); Dane Mealey, Somers, CT (US); Brian McCarthy, East Longmeadow, MA (US); Ben Ross-Johnsrud, Wilbraham, MA (US); Kedar Chitale, Newton, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/690,263

(22) Filed: Aug. 29, 2017

(65) Prior Publication Data

US 2018/0015392 A1 Jan. 18, 2018

Related U.S. Application Data

(63) Continuation of application No. 15/249,129, filed on Aug. 26, 2016, now Pat. No. 9,744,483, which is a
(Continued)

(51) Int. Cl.
*C02F 1/36* (2006.01)
*B01D 21/28* (2006.01)
(Continued)

(52) U.S. Cl.
CPC ....... *B01D 21/283* (2013.01); *B01D 21/0042* (2013.01); *B01D 21/0045* (2013.01);
(Continued)

(58) Field of Classification Search
CPC ...... B01D 29/115; B01D 37/00; B01D 29/52; B01D 29/865; B01D 2201/0415;
(Continued)

(56) References Cited

U.S. PATENT DOCUMENTS

| 2,473,971 A | 6/1949 | Ross |
| 2,667,944 A | 2/1954 | Crites |

(Continued)

FOREIGN PATENT DOCUMENTS

| AU | 2002236405 | 9/2002 |
| CN | 105 087 788 A | 11/2015 |

(Continued)

OTHER PUBLICATIONS

Alvarez et al.; Shock Waves, vol. 17, No. 6, pp. 441-447, 2008.
(Continued)

*Primary Examiner* — Walter D. Griffin
*Assistant Examiner* — Cameron J Allen
(74) *Attorney, Agent, or Firm* — FloDesign Sonics, Inc.

(57) ABSTRACT

Devices for separating a host fluid from a second fluid or particulate are disclosed. The devices include an acoustic chamber, a fluid outlet at a top end of the acoustic chamber, a concentrate outlet at a bottom end of the acoustic chamber, and an inlet on a first side end of the acoustic chamber. An ultrasonic transducer and reflector create a multi-dimensional acoustic standing wave in the acoustic chamber that traps and separates particulates (e.g. cells) from a host fluid. The host fluid is collected via the fluid outlet, and the particulates are collected via the concentrate outlet. The
(Continued)

device is a large-scale device that is able to process liters/hour, and has a large interior volume.

16 Claims, 27 Drawing Sheets

Related U.S. Application Data continuation-in-part of application No. 14/791,115, filed on Jul. 2, 2015, now Pat. No. 9,827,511.

(60) Provisional application No. 62/020,088, filed on Jul. 2, 2014, provisional application No. 62/154,672, filed on Apr. 29, 2015, provisional application No. 62/211,142, filed on Aug. 28, 2015, provisional application No. 62/252,068, filed on Nov. 6, 2015.

(51) Int. Cl.
*B01D 21/00* (2006.01)
*C12M 1/00* (2006.01)
*B06B 1/06* (2006.01)
*B01D 21/24* (2006.01)

(52) U.S. Cl.
CPC ..... *B01D 21/0087* (2013.01); *B01D 21/2422* (2013.01); *B06B 1/06* (2013.01); *C02F 1/36* (2013.01); *C12M 47/02* (2013.01)

(58) Field of Classification Search
CPC ...... B01D 2201/0446; B01D 2201/127; B01D 17/04; B01D 17/06; B01D 21/283; C12M 47/02; C12M 29/18; C12M 29/10; C12M 33/08; C12M 35/04; C12N 13/00; C12N 1/02; B06B 1/0644; H01L 41/0973
See application file for complete search history.

(56) References Cited

U.S. PATENT DOCUMENTS

| | | | |
|---|---|---|---|
| 3,372,370 A | 3/1968 | Cyr | |
| 3,555,311 A | 1/1971 | Weber | |
| 4,055,491 A | 10/1977 | Porath-Furedi | |
| 4,065,875 A | 1/1978 | Srna | |
| 4,118,649 A | 10/1978 | Schwartzman et al. | |
| 4,158,629 A | 6/1979 | Sawyer | |
| 4,165,273 A | 8/1979 | Azarov et al. | |
| 4,173,725 A | 11/1979 | Asai et al. | |
| 4,204,096 A | 5/1980 | Barcus et al. | |
| 4,254,661 A | 3/1981 | Kossoff et al. | |
| 4,320,659 A | 3/1982 | Lynnworth et al. | |
| 4,344,448 A | 8/1982 | Potts | |
| 4,398,325 A | 8/1983 | Piaget et al. | |
| 4,484,907 A | 11/1984 | Sheeran, Jr. | |
| 4,552,669 A | 11/1985 | Sekellick | |
| 4,666,595 A | 5/1987 | Graham | |
| 4,673,512 A | 6/1987 | Schram | |
| 4,699,588 A | 10/1987 | Zinn et al. | |
| 4,743,361 A | 5/1988 | Schram | |
| 4,759,775 A | 7/1988 | Peterson et al. | |
| 4,800,316 A | 1/1989 | Wang | |
| 4,821,838 A | 4/1989 | Chen | |
| 4,836,684 A | 6/1989 | Javorik et al. | |
| 4,860,993 A | 8/1989 | Goode | |
| 4,878,210 A | 10/1989 | Mitome | |
| 4,983,189 A | 1/1991 | Peterson et al. | |
| 5,059,811 A | 10/1991 | King et al. | |
| 5,062,965 A | 11/1991 | Bernou et al. | |
| 5,085,783 A | 2/1992 | Feke et al. | |
| 5,164,094 A | 11/1992 | Stuckart | |
| 5,225,089 A | 7/1993 | Benes et al. | |
| 5,371,429 A | 12/1994 | Manna | |
| 5,395,592 A | 3/1995 | Bolleman et al. | |
| 5,431,817 A | 7/1995 | Braatz et al. | |
| 5,443,985 A | 8/1995 | Lu et al. | |
| 5,452,267 A | 9/1995 | Spevak | |
| 5,475,486 A | 12/1995 | Paoli | |
| 5,484,537 A | 1/1996 | Whitworth | |
| 5,527,460 A | 6/1996 | Trampler et al. | |
| 5,560,362 A | 10/1996 | Sliwa, Jr. et al. | |
| 5,562,823 A | 10/1996 | Reeves | |
| 5,594,165 A | 1/1997 | Madanshetty | |
| 5,604,301 A | 2/1997 | Mountford et al. | |
| 5,626,767 A | 5/1997 | Trampler et al. | |
| 5,688,405 A | 11/1997 | Dickinson et al. | |
| 5,711,888 A * | 1/1998 | Trampler | B01D 21/283 210/748.05 |
| 5,831,166 A | 11/1998 | Kozuka et al. | |
| 5,834,871 A | 11/1998 | Puskas | |
| 5,902,489 A | 5/1999 | Yasuda et al. | |
| 5,912,182 A | 6/1999 | Coakley et al. | |
| 5,947,299 A | 9/1999 | Vazquez et al. | |
| 5,951,456 A | 9/1999 | Scott | |
| 6,090,295 A | 6/2000 | Raghavarao et al. | |
| 6,166,231 A | 12/2000 | Hoeksema | |
| 6,216,538 B1 | 4/2001 | Yasuda et al. | |
| 6,205,848 B1 | 6/2001 | Faber et al. | |
| 6,273,262 B1 | 8/2001 | Yasuda et al. | |
| 6,332,541 B1 | 12/2001 | Coakley et al. | |
| 6,391,653 B1 | 5/2002 | Letcher et al. | |
| 6,475,151 B2 | 11/2002 | Koger et al. | |
| 6,482,327 B1 | 11/2002 | Mori et al. | |
| 6,487,095 B1 | 11/2002 | Malik et al. | |
| 6,592,821 B1 | 7/2003 | Wada et al. | |
| 6,641,708 B1 | 11/2003 | Becker et al. | |
| 6,649,069 B2 | 11/2003 | DeAngelis | |
| 6,699,711 B1 | 3/2004 | Hahn et al. | |
| 6,727,451 B1 | 4/2004 | Fuhr et al. | |
| 6,763,722 B2 | 7/2004 | Fjield et al. | |
| 6,881,314 B1 | 4/2005 | Wang et al. | |
| 6,929,750 B2 | 8/2005 | Laurell et al. | |
| 6,936,151 B1 | 8/2005 | Lock et al. | |
| 7,008,540 B2 | 3/2006 | Weavers et al. | |
| 7,010,979 B2 | 3/2006 | Scott | |
| 7,061,163 B2 | 6/2006 | Nagahara et al. | |
| 7,081,192 B1 | 7/2006 | Wang et al. | |
| 7,093,482 B2 | 8/2006 | Berndt | |
| 7,108,137 B2 | 9/2006 | Lal et al. | |
| 7,150,779 B2 | 12/2006 | Meegan, Jr. | |
| 7,186,502 B2 | 3/2007 | Vesey | |
| 7,191,787 B1 | 3/2007 | Redeker et al. | |
| 7,322,431 B2 | 1/2008 | Ratcliff | |
| 7,331,233 B2 | 2/2008 | Scott | |
| 7,340,957 B2 | 3/2008 | Kaduchak et al. | |
| 7,373,805 B2 | 5/2008 | Hawkes et al. | |
| 7,541,166 B2 | 6/2009 | Belgrader et al. | |
| 7,601,267 B2 | 10/2009 | Haake et al. | |
| 7,673,516 B2 | 3/2010 | Janssen et al. | |
| 7,674,630 B2 | 3/2010 | Siversson | |
| 7,837,040 B2 | 11/2010 | Ward et al. | |
| 7,846,382 B2 | 12/2010 | Strand et al. | |
| 7,968,049 B2 | 6/2011 | Takahashi et al. | |
| 8,075,786 B2 | 12/2011 | Bagajewicz | |
| 8,080,202 B2 | 12/2011 | Takahashi et al. | |
| 8,134,705 B2 | 3/2012 | Kaduchak et al. | |
| 8,256,076 B1 | 9/2012 | Feller | |
| 8,266,950 B2 | 9/2012 | Kaduchak et al. | |
| 8,273,253 B2 | 9/2012 | Curran | |
| 8,273,302 B2 | 9/2012 | Takahashi et al. | |
| 8,309,408 B2 | 11/2012 | Ward et al. | |
| 8,319,398 B2 | 11/2012 | Vivek et al. | |
| 8,334,133 B2 | 12/2012 | Fedorov et al. | |
| 8,387,803 B2 | 3/2013 | Thorslund et al. | |
| 8,592,204 B2 | 11/2013 | Lipkens et al. | |
| 8,679,338 B2 | 3/2014 | Rietman et al. | |
| 8,691,145 B2 | 4/2014 | Dionne et al. | |
| 8,873,051 B2 | 10/2014 | Kaduchak et al. | |
| 8,889,388 B2 | 11/2014 | Wang et al. | |
| 9,272,234 B2 | 3/2016 | Lipkens et al. | |
| 9,357,293 B2 | 5/2016 | Claussen | |
| 9,365,815 B2 | 6/2016 | Miyazaki et al. | |
| 9,368,110 B1 | 6/2016 | Hershey et al. | |
| 9,388,363 B2 | 7/2016 | Goodson et al. | |

(56) References Cited

U.S. PATENT DOCUMENTS

| | | |
|---|---|---|
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 9,532,769 B2 | 1/2017 | Dayton et al. |
| 9,533,241 B2 | 1/2017 | Presz, Jr. et al. |
| 9,550,134 B2 | 1/2017 | Lipkens et al. |
| 9,550,998 B2 | 1/2017 | Williams |
| 9,556,271 B2 | 1/2017 | Blumberg et al. |
| 9,556,411 B2 | 1/2017 | Lipkens et al. |
| 9,566,352 B2 | 2/2017 | Holmes et al. |
| 9,567,559 B2 | 2/2017 | Lipkens et al. |
| 9,567,609 B2 | 2/2017 | Paschon et al. |
| 9,572,897 B2 | 2/2017 | Bancel et al. |
| 9,573,995 B2 | 2/2017 | Schurpf et al. |
| 9,574,014 B2 | 2/2017 | Williams et al. |
| 9,580,500 B2 | 2/2017 | Schurpf et al. |
| 9,587,003 B2 | 3/2017 | Bancel et al. |
| 9,597,357 B2 | 3/2017 | Gregory et al. |
| 9,597,380 B2 | 3/2017 | Chakraborty et al. |
| 9,605,074 B2 | 3/2017 | Shah |
| 9,605,266 B2 | 3/2017 | Rossi et al. |
| 9,606,086 B2 | 3/2017 | Ding et al. |
| 9,608,547 B2 | 3/2017 | Ding et al. |
| 9,611,465 B2 | 4/2017 | Handa et al. |
| 9,616,090 B2 | 4/2017 | Conway et al. |
| 9,623,348 B2 | 4/2017 | McCarthy et al. |
| 9,629,877 B2 | 4/2017 | Cooper et al. |
| D787,630 S | 5/2017 | Lipkens et al. |
| 9,644,180 B2 | 5/2017 | Kahvejian et al. |
| 9,645,060 B2 | 5/2017 | Fiering |
| 9,656,263 B2 | 5/2017 | Laurell et al. |
| 9,657,290 B2 | 5/2017 | Dimov et al. |
| 9,662,375 B2 | 5/2017 | Jensen et al. |
| 9,663,756 B1 | 5/2017 | Lipkens et al. |
| 9,670,477 B2 | 6/2017 | Lipkens et al. |
| 9,670,938 B2 | 6/2017 | Beliavsky |
| 9,675,668 B2 | 6/2017 | Bancel et al. |
| 9,675,902 B2 | 6/2017 | Lipkens et al. |
| 9,675,906 B2 | 6/2017 | Lipkens et al. |
| 9,677,055 B2 | 6/2017 | Jones et al. |
| 9,685,155 B2 | 6/2017 | Hershey et al. |
| 9,686,096 B2 | 6/2017 | Lipkens et al. |
| 9,688,958 B2 | 6/2017 | Kennedy, III et al. |
| 9,689,234 B2 | 6/2017 | Gregory et al. |
| 9,689,802 B2 | 6/2017 | Caseres et al. |
| 9,695,063 B2 | 7/2017 | Rietman et al. |
| 9,695,442 B2 | 7/2017 | Guschin et al. |
| 9,810,665 B2 | 11/2017 | Fernald et al. |
| 9,833,763 B2 | 12/2017 | Fernald et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1* | 2/2006 | Strand .................. B01D 21/283 210/748.05 |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0207225 A1 | 8/2011 | Mehta et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1* | 12/2012 | Dionne .................. B06B 1/0625 422/128 |
| 2012/0329122 A1 | 12/2012 | Lipkens et al. |
| 2013/0017577 A1 | 1/2013 | Arunakumari et al. |

(56) References Cited

U.S. PATENT DOCUMENTS

| | | |
|---|---|---|
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1* | 10/2013 | Dutra ................ A61M 1/3681 210/748.02 |
| 2013/0277317 A1 | 10/2013 | LoRicco et al. |
| 2013/0284271 A1 | 10/2013 | Lipkens et al. |
| 2014/0011240 A1* | 1/2014 | Lipkens ................ B01D 21/28 435/71.1 |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0154795 A1 | 6/2014 | Lipkens et al. |
| 2014/0319077 A1 | 10/2014 | Lipkens et al. |
| 2014/0329997 A1 | 11/2014 | Kennedy, III et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0252317 A1 | 9/2015 | Lipkens et al. |
| 2015/0274550 A1 | 10/2015 | Lipkens et al. |
| 2015/0321129 A1 | 11/2015 | Lipkens et al. |
| 2016/0060615 A1 | 3/2016 | Walther et al. |
| 2016/0089620 A1 | 3/2016 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325039 A1 | 11/2016 | Leach et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2016/0368000 A1 | 12/2016 | Dionne et al. |
| 2016/0369236 A1 | 12/2016 | Kennedy, III et al. |
| 2016/0370326 A9 | 12/2016 | Kaduchak et al. |
| 2017/0000413 A1 | 1/2017 | Clymer et al. |
| 2017/0002060 A1 | 1/2017 | Bolen et al. |
| 2017/0002839 A1 | 1/2017 | Burkland et al. |
| 2017/0007679 A1 | 1/2017 | Maeder et al. |
| 2017/0008029 A1 | 1/2017 | Lipkens et al. |
| 2017/0016025 A1 | 1/2017 | Poirot et al. |
| 2017/0016027 A1 | 1/2017 | Lee et al. |
| 2017/0020926 A1 | 1/2017 | Mata-Fink et al. |
| 2017/0029802 A1 | 2/2017 | Lipkens et al. |
| 2017/0035866 A1 | 2/2017 | Poirot et al. |
| 2017/0037386 A1 | 2/2017 | Jones et al. |
| 2017/0038288 A1 | 2/2017 | Ward et al. |
| 2017/0042770 A1 | 2/2017 | Warner et al. |
| 2017/0044517 A1 | 2/2017 | Lipkens et al. |
| 2017/0049949 A1 | 2/2017 | Gilmanshin et al. |
| 2017/0056448 A1 | 3/2017 | Glick et al. |
| 2017/0058036 A1 | 3/2017 | Ruiz-Opazo et al. |
| 2017/0065636 A1 | 3/2017 | Moriarty et al. |
| 2017/0066015 A1 | 3/2017 | Lipkens et al. |
| 2017/0067021 A1 | 3/2017 | Moriarty et al. |
| 2017/0067022 A1 | 3/2017 | Poirot et al. |
| 2017/0072405 A1 | 3/2017 | Mao et al. |
| 2017/0073406 A1 | 3/2017 | Schurpf et al. |
| 2017/0073423 A1 | 3/2017 | Juillerat et al. |
| 2017/0073638 A1 | 3/2017 | Campana et al. |
| 2017/0073684 A1 | 3/2017 | Rossi et al. |
| 2017/0073685 A1 | 3/2017 | Maeder et al. |
| 2017/0080070 A1 | 3/2017 | Weinschenk et al. |
| 2017/0081629 A1 | 3/2017 | Lipkens et al. |
| 2017/0088809 A1 | 3/2017 | Lipkens et al. |
| 2017/0088844 A1 | 3/2017 | Williams |
| 2017/0089826 A1 | 3/2017 | Lin |
| 2017/0096455 A1 | 4/2017 | Baric et al. |
| 2017/0107536 A1 | 4/2017 | Zhang et al. |
| 2017/0107539 A1 | 4/2017 | Yu et al. |
| 2017/0119820 A1 | 5/2017 | Moriarty et al. |
| 2017/0128523 A1 | 5/2017 | Ghatnekar et al. |
| 2017/0128857 A1 | 5/2017 | Lipkens et al. |
| 2017/0130200 A1 | 5/2017 | Moriarty et al. |
| 2017/0136168 A1 | 5/2017 | Spain et al. |
| 2017/0137491 A1 | 5/2017 | Matheson et al. |
| 2017/0137774 A1 | 5/2017 | Lipkens et al. |
| 2017/0137775 A1 | 5/2017 | Lipkens et al. |
| 2017/0137802 A1 | 5/2017 | Lipkens et al. |
| 2017/0145094 A1 | 5/2017 | Galetto |
| 2017/0151345 A1 | 6/2017 | Shah |
| 2017/0152502 A1 | 6/2017 | Scharenberg et al. |
| 2017/0152503 A1 | 6/2017 | Scharenberg et al. |
| 2017/0152504 A1 | 6/2017 | Scharenberg et al. |
| 2017/0152505 A1 | 6/2017 | Scharenberg et al. |
| 2017/0152527 A1 | 6/2017 | Paschon et al. |
| 2017/0152528 A1 | 6/2017 | Zhang et al. |
| 2017/0158749 A1 | 6/2017 | Cooper et al. |
| 2017/0159005 A1 | 6/2017 | Lipkens et al. |
| 2017/0159007 A1 | 6/2017 | Lipkens et al. |
| 2017/0166860 A1 | 6/2017 | Presz, Jr. et al. |
| 2017/0166877 A1 | 6/2017 | Bayle et al. |
| 2017/0166878 A9 | 6/2017 | Thanos et al. |
| 2017/0166903 A1 | 6/2017 | Zhang et al. |
| 2017/0173080 A1 | 6/2017 | Lee et al. |
| 2017/0173128 A1 | 6/2017 | Hoge et al. |
| 2017/0173498 A9 | 6/2017 | Lipkens et al. |
| 2017/0175073 A1 | 6/2017 | Lipkens et al. |
| 2017/0175125 A1 | 6/2017 | Welstead et al. |
| 2017/0175139 A1 | 6/2017 | Wu et al. |
| 2017/0175144 A1 | 6/2017 | Zhang et al. |
| 2017/0175509 A1 | 6/2017 | Abdel-Fattah et al. |
| 2017/0175720 A1 | 6/2017 | Tang et al. |
| 2017/0183390 A1 | 6/2017 | Springer et al. |
| 2017/0183413 A1 | 6/2017 | Galetto |
| 2017/0183418 A1 | 6/2017 | Galetto |
| 2017/0183420 A1 | 6/2017 | Gregory et al. |
| 2017/0184486 A1 | 6/2017 | Mach et al. |
| 2017/0189450 A1 | 7/2017 | Conway et al. |
| 2017/0190767 A1 | 7/2017 | Schurpf et al. |
| 2017/0191022 A1 | 7/2017 | Lipkens et al. |
| 2017/0232439 A1 | 8/2017 | Suresh et al. |

FOREIGN PATENT DOCUMENTS

| | | |
|---|---|---|
| CN | 104722106 B | 4/2016 |
| DE | 30 27 433 A1 | 2/1982 |
| DE | 32 18 488 A1 | 11/1983 |
| DE | 196 48 519 A1 | 6/1998 |
| DE | 103 19 467 B3 | 7/2004 |
| DE | 10 2008 006 501 A1 | 9/2008 |
| DE | 10 2014 206 823 A1 | 10/2015 |
| EP | 0 292 470 B1 | 11/1988 |
| EP | 0 167 406 B1 | 7/1991 |
| EP | 0 641 606 | 3/1995 |
| EP | 1 175 931 A1 | 1/2002 |
| EP | 1 254 669 B1 | 11/2002 |
| EP | 1 308 724 A2 | 5/2003 |
| EP | 2 209 545 | 7/2010 |
| GB | 2 420 510 A | 5/2006 |
| JP | 9-136090 | 5/1997 |
| KR | 1442486 | 9/2014 |
| RU | 2085933 | 7/1997 |
| SU | 629496 | 10/1978 |
| WO | WO 1987/07178 A1 | 12/1987 |
| WO | WO 89/11899 A1 | 12/1989 |

(56) References Cited

FOREIGN PATENT DOCUMENTS

| WO | WO 90/05008 | 3/1990 |
|---|---|---|
| WO | WO 95/01214 A1 | 1/1995 |
| WO | WO 97/34643 | 9/1997 |
| WO | WO 1998/017373 | 4/1998 |
| WO | WO 98/50133 A1 | 11/1998 |
| WO | WO 00/41794 | 7/2000 |
| WO | WO 02/072234 A1 | 9/2002 |
| WO | WO 02/072236 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |
| WO | WO 2011/161463 A2 | 12/2011 |
| WO | WO 2013/043044 A1 | 3/2013 |
| WO | WO 2013/043297 A1 | 3/2013 |
| WO | WO 2013/049623 A1 | 4/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/046605 A1 | 3/2014 |
| WO | WO 2014/055219 A2 | 4/2014 |
| WO | WO 2014/124306 A1 | 8/2014 |
| WO | WO 2014/153651 | 10/2014 |
| WO | WO 2015/006730 | 1/2015 |
| WO | WO 2015/102528 | 7/2015 |
| WO | WO 2016/004398 A2 | 1/2016 |
| WO | WO 2016/124542 | 8/2016 |
| WO | hWO 2016/176663 A1 | 11/2016 |
| WO | WO 2016/209082 | 12/2016 |
| WO | WO 2017/041102 A1 | 3/2017 |

OTHER PUBLICATIONS

Augustsson et al., Acoustophoretic microfluidic chip for sequential elution of surface bound molecules from beads or cells, Biomicrofluidics, Sep. 2012, 6(3):34115.

Benes et al.; Ultrasonic Separation of Suspended Particles, 2001 IEEE Ultrasonics Symposium; Oct. 7-10, 2001; pp. 649-659; Atlanta, Georgia.

Castilho et al.; Animal Cell Technology: From Biopharmaceuticals to Gene Therapy; 11—Animal Cell Separation; 2008.

Castro; Tunable gap and quantum quench dynamics in bilayer graphene; Jul. 13, 2010; Mathematica Summer School.

Chitale et al.; Understanding the Fluid Dynamics Associated with Macro Scale Ultrasonic Separators; Proceedings of Meetings on Acoustics, May 2015.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Grenvall et al.; Concurrent Isolation of Lymphocytes and Granulocytes Using Prefocused Free Flow Acoustophoresis; Analytical Chemistry; vol. 87; pp. 5596-5604; 2015.

Higginson et al.; Tunable optics derived from nonlinear acoustic effects; Journal of Applied Physics; vol. 95; No. 10; pp. 5896-5904; 2004.

Hill et al.; Ultrasonic Particle Manipulation; Microfluidic Technologies for Miniaturized Analysis Systems, Jan. 2007, pp. 359-378.

Ilinskii et al.; Acoustic Radiation Force on a Sphere in Tissue; AIP Conference Proceedings; 2012.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Li et al.; Electromechanical behavior of PZT-brass unimorphs; J. Am. Ceram. Soc. vol. 82; No. 7; pp. 1733-1740, 1999.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; Separation of bacterial spores from flowering water in macro-scale cavities by ultrasonic standing waves; submitted/uploaded to http://arxiv.org/abs/1006.5467 on Jun. 28, 2010.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et al.; An Industrial-Prototype Acoustic Array for Real-Time Emulsion Layer Detection in Oil Storage Tanks; IEEE Sensors Journal, vol. 9, No. 12, Dec. 2009.

Musiak et al.; Design of a Control System for Acoustophoretic Separation, 2013 IEEE 56$^{th}$ International Midwest Symposium on Circuits and Systems (MWSCAS), Aug. 2013, pp. 1120-1123.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

phys. org. "Engineers develop revolutionary nanotech water desalination membrane." Nov. 6, 2006. http://phys.org/news82047372.html.

Ponomarenko et al.; Density of states and zero Landau level probed through capacitance of graphene; Nature Nanotechnology Letters, Jul. 5, 2009; DOI: 10.1038/NNANO.2009.177.

"Proceedings of the Acoustics 2012 Nantes Conference," Apr. 23-27, 2012, Nantes, France, pp. 278-282.

Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.

Seymour et al, J. Chem. Edu., 1990, 67(9), p. 763, published Sep. 1990.

Volpin et al.; Mesh simplification with smooth surface reconstruction; Computer-Aided Design; vol. 30; No. 11; 1998.

Wang et al.; Retention and Viability Characteristics of Mammalian Cells in an Acoustically Driven Polymer Mesh; Biotechnol. Prog. 2004, pp. 384-387 (2004).

Wicklund et al.; Ultrasonic Manipulation of Single Cells; Methods in Molecular Biology; vol. 853; pp. 1777-196; 2012.

Annex to Form PCT/ISA/206—Communication Relating to the Results of the Partial International Search Report dated Jul. 18, 2013.

European Search Report of European Application No. 11769474.5 dated Sep. 5, 2013.

European Search Report of European Application No. 11796470.0 dated Jan. 5, 2016.

(56) References Cited

OTHER PUBLICATIONS

European Search Report of European Application No. 13760840.2, dated Feb. 4, 2016.
European Search Report of European Application No. 13721179.3 dated Mar. 23, 2016.
European Search Report for European Application No. 14749278.9 dated Jan. 13, 2017.
Extended European Search Report for European Application No. EP 12833859.7 dated Mar. 20, 2015.
Extended European Search Report for European Application No. EP 14787587.6 dated Jan. 2, 2017.
International Search Report and Written Opinion for International Application No. PCT/US2011/032181 dated Dec. 20, 2011.
International Search Report and Written Opinion for International Application No. PCT/US2011/040787 dated Feb. 27, 2012.
International Search Report and Written Opinion for International Application No. PCT/US2012/051804 dated Nov. 16, 2012.
International Search Report and Written Opinion for International Application No. PCT/US2013/037404 dated Jun. 21, 2013.
International Search Report and Written Opinion for International Application No. PCT/US2013/032705 dated Jul. 26, 2013.
International Search Report and Written Opinion for International Application No. PCT/US2013/050729 dated Sep. 25, 2013.
International Search Report and Written Opinion for International Application No. PCT/US2013/059640 dated Feb. 18, 2014.
International Search Report and Written Opinion for International Application No. PCT/US2014/015382 dated May 6, 2014.
International Search Report and Written Opinion for International Application No. PCT/US2014/035557 dated Aug. 27, 2014.
International Search Report and Written Opinion for International Application No. PCT/US2014/043930 dated Oct. 22, 2014.
International Search Report and Written Opinion for International Application No. PCT/US2014/046412 dated Oct. 27, 2014.
International Search Report and Written Opinion for International Application No. PCT/US2014/064088 dated Jan. 30, 2015.
International Search Report and Written Opinion for International Application No. PCT/US2015/010595 dated Apr. 15, 2015.
International Search Report and Written Opinion for International Application No. PCT/US2015/019755 dated May 4, 2015.
International Search Report and Written Opinion for International Application No. PCT/US2015/030009 dated Jul. 30, 2015.
International Search Report and Written Opinion for International Application No. PCT/US2015/039125 dated Sep. 30, 2015.
International Search Report and Written Opinion for International Application No. PCT/US2015/053200 dated Dec. 28, 2015.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/038233 dated Sep. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/044586 dated Oct. 21, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
International Search Report and Written Opinion for International Application No. PCT/US2017/015197 dated Apr. 3, 2017.
International Search Report and Written Opinion for International Application No. PCT/US2017/015450 dated Apr. 10, 2017.
International Search Report and Written Opinion for International Application No. PCT/US2016/047217 dated Apr. 11, 2017.
International Search Report and Written Opinion for International Application No. PCT/US2016/048243 dated Apr. 20, 2017.
International Search Report and Written Opinion for International Application No. PCT/US2017/017788 dated May 8, 2017.
International Search Report and Written Opinion for International Application No. PCT/US2017/030903 dated Jul. 19, 2017.
International Search Report and Written Opinion for International Application No. PCT/US2017/025108 dated Jul. 20, 2017.
International Search Report and Written Opinion for International Application No. PCT/US2017/031425 dated Aug. 30, 2017.
Sony New Release: <http://www.sony.net/SonyInfo/News/Press/201010/10-137E/index.html>.

* cited by examiner

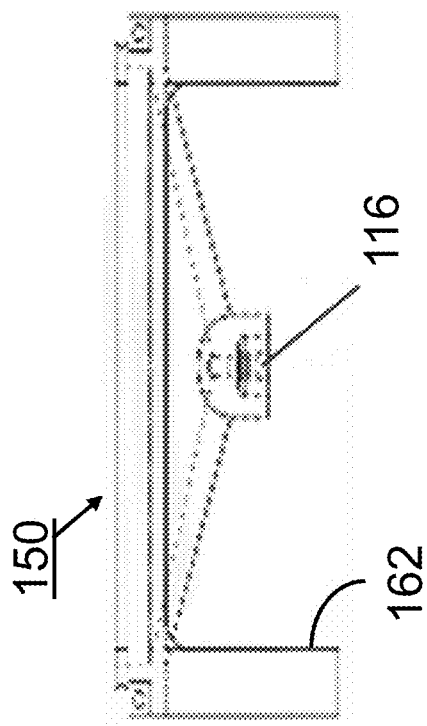
FIG. 4A
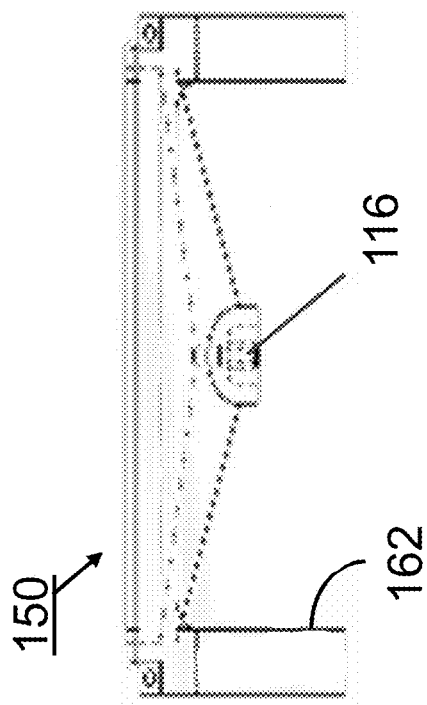
FIG. 4B
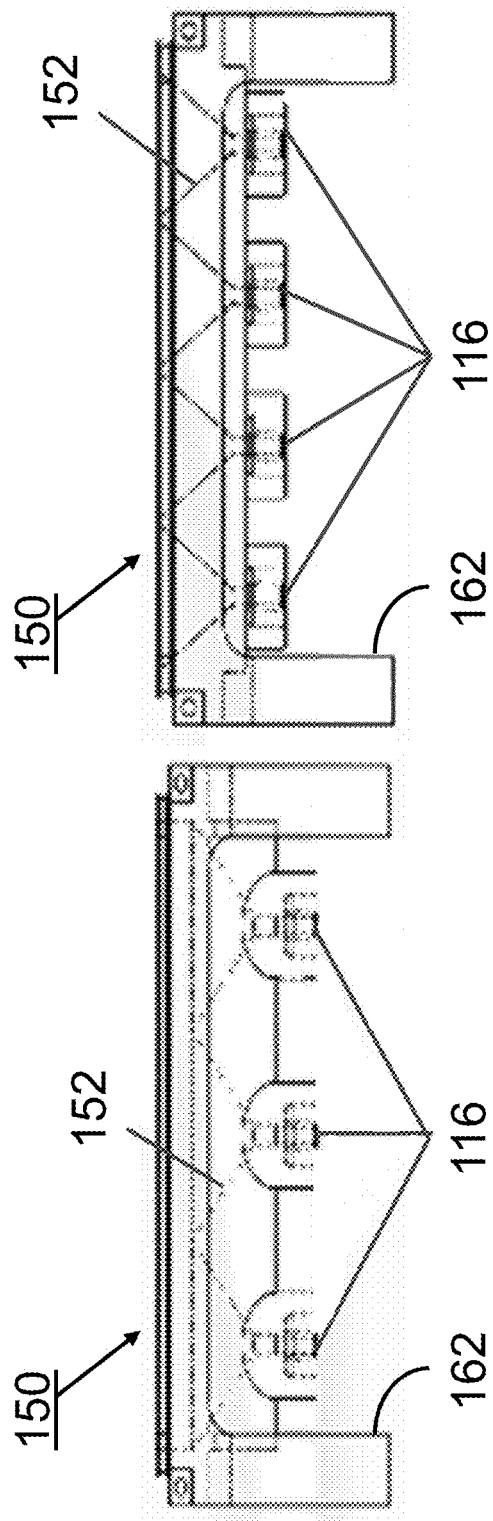
FIG. 4C
FIG. 4D

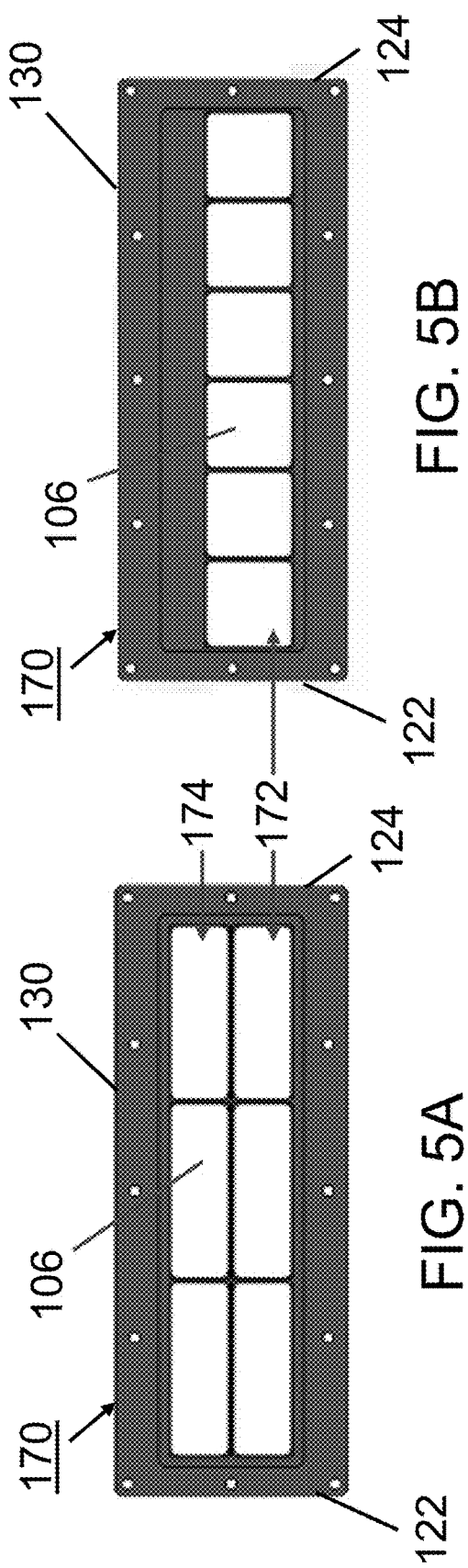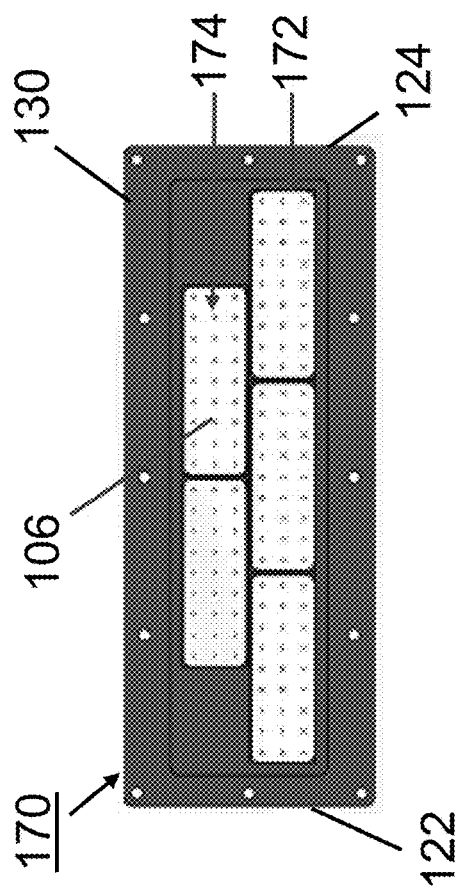

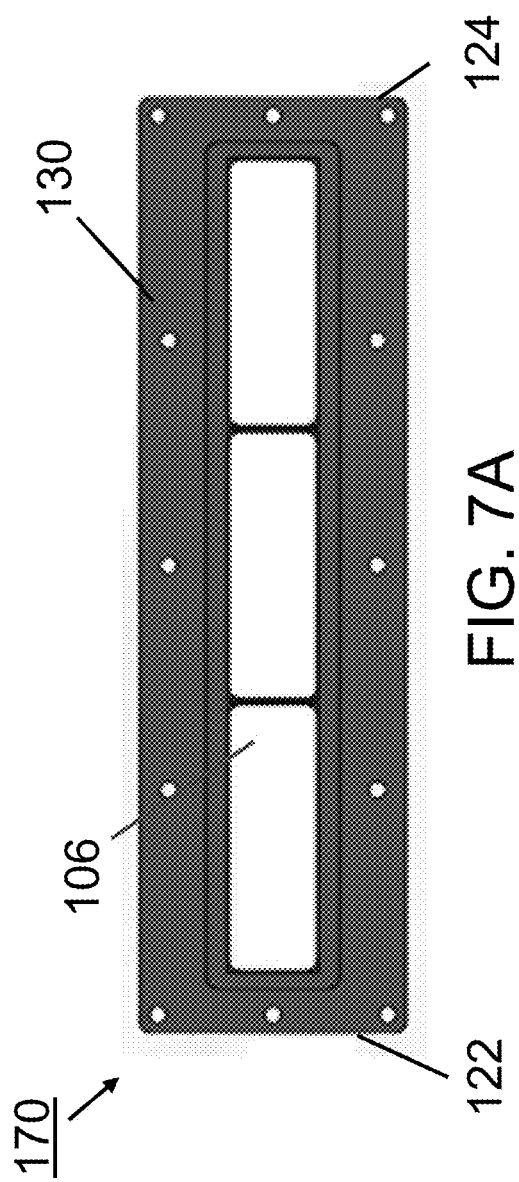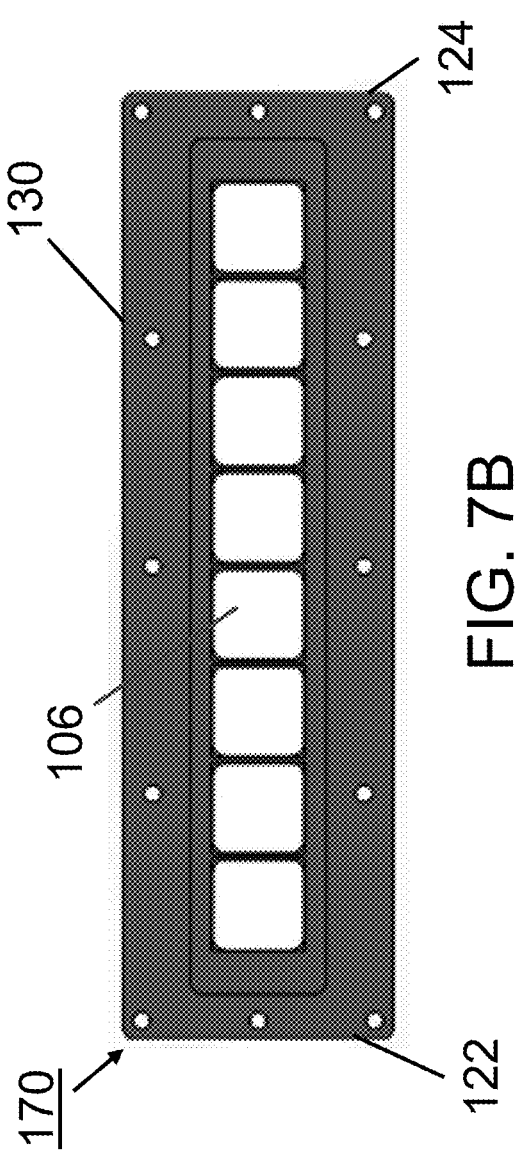

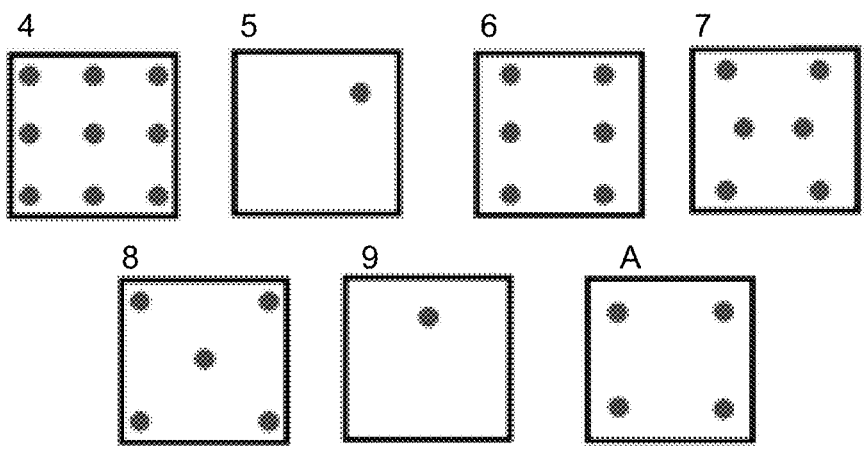
FIG. 28A
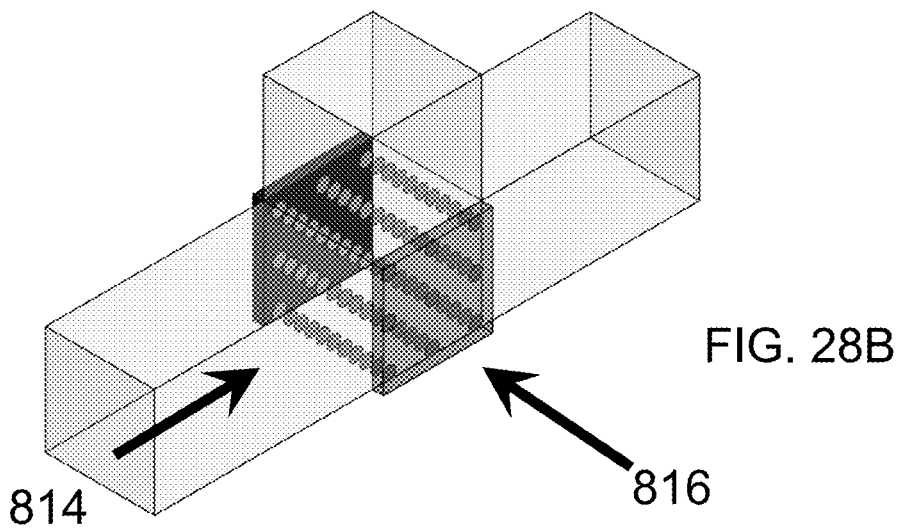
FIG. 28B
FIG. 28C
FIG. 28D
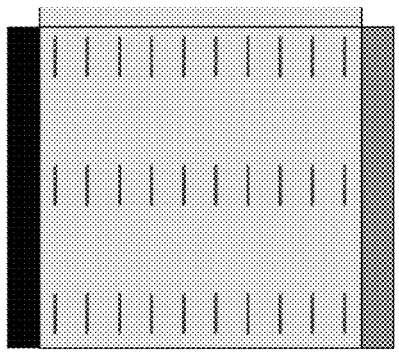
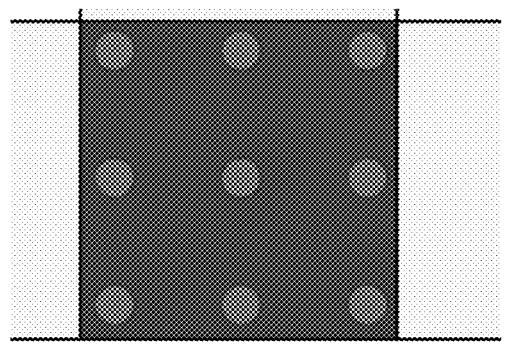

LARGE SCALE ACOUSTIC SEPARATION DEVICE

CROSS-REFERENCE TO RELATED APPLICATIONS

This application is a continuation of U.S. patent application Ser. No. 15/249,129, filed on Aug. 26, 2016, which claims the benefit of U.S. Provisional Patent Application Ser. No. 62/211,142, filed on Aug. 28, 2015; and which claims the benefit of U.S. Provisional Patent Application Ser. No. 62/252,068, filed on Nov. 6, 2015, and which is also a continuation-in-part of U.S. patent application Ser. No. 14/791,115, filed Jul. 2, 2015, which claims the benefit of U.S. Provisional Patent Application Ser. No. 62/020,088, filed on Jul. 2, 2014; and which claims the benefit of U.S. Provisional Patent Application Ser. No. 62/154,672, filed on Apr. 29, 2015. The entire disclosures of all of the above applications are hereby fully incorporated herein by reference.

BACKGROUND

Acoustophoresis is the separation of particles and secondary fluids from a primary or host fluid using high intensity acoustic standing waves, and without the use of membranes or physical size exclusion filters. It has been known that high intensity standing waves of sound can exert forces on particles in a fluid when there is a differential in both density and/or compressibility, otherwise known as the acoustic contrast factor. The pressure profile in a standing wave contains areas of local minimum pressure amplitudes at its nodes and local maxima at its anti-nodes. Depending on the density and compressibility of the particles, they will be trapped at the nodes or anti-nodes of the standing wave. Generally, the higher the frequency of the standing wave, the smaller the particles that can be trapped due the pressure of the standing wave.

The separation of materials (e.g., acoustic separation of secondary fluids from primary fluids or particles from a primary fluid stream) that have different acoustic contrast factors (a combination of density and the speed of sound through the material) has been demonstrated at the MEMS (micro electrical mechanical systems) scale. At the MEMS scale, conventional acoustophoresis systems rely on using half or quarter wavelength acoustic chambers, which at frequencies of a few megahertz are typically less than a millimeter in thickness, and operate at very slow flow rates (e.g., 4/min). Such systems are not scalable since they benefit from extremely low Reynolds number, laminar flow operation, and require minimal fluid dynamic optimization.

At the macro-scale, planar acoustic standing waves have been used to accomplish this separation process. However, a single planar wave tends to trap the particles or secondary fluid in a manner such that they can only be separated from the primary fluid by turning off the planar standing wave. This does not allow for continuous operation. Also, the amount of power that is needed to generate the acoustic planar standing wave tends to heat the primary fluid through waste energy.

Conventional acoustophoresis devices have thus had limited efficacy due to several factors including heat generation, use of planar standing waves, limits on fluid flow, and the inability to capture different types of materials. It would therefore be desirable to provide systems and methods of generating optimized particle clusters to improve gravity separation and collection efficiency. Improved acoustophoresis devices using improved fluid dynamics would also be desirable, so the acoustophoresis can be a continuous process.

BRIEF DESCRIPTION

The present disclosure relates, in various embodiments, to macro-scale acoustophoretic devices with improved fluid dynamics that can be used to improve the separation of particles (e.g. cells) from a particle/fluid mixture. More particularly, the devices include an acoustic chamber containing an ultrasonic transducer and a reflector that set up a multi-dimensional acoustic standing wave.

Disclosed herein are acoustophoresis devices for separating a primary/host fluid from a secondary fluid or particulate. For example, the particulate may be cells such as Chinese hamster ovary (CHO) cells, NS0 hybridoma cells, baby hamster kidney (BHK) cells, or human cells; lymphocytes such as T cells (e.g., regulatory T-cells (Tregs), Jurkat T-cells), B cells, or NK cells; their precursors, such as peripheral blood mononuclear cells (PBMCs); algae or other plant cells, bacteria, viruses, or microcarriers.

Disclosed in various embodiments are acoustophoretic devices, comprising: an acoustic chamber that includes at least one inlet at a first end thereof; at least one fluid outlet at a top end of the acoustophoretic device; at least one concentrate outlet at a bottom end of the acoustophoretic device; at least one ultrasonic transducer coupled to the acoustic chamber, the at least one ultrasonic transducer including a piezoelectric material configured to be driven by a voltage signal to create a multi-dimensional acoustic standing wave in the acoustic chamber; and a reflector across the acoustic chamber from the at least one ultrasonic transducer; wherein the acoustic chamber includes a plan cross-sectional area defined by a length and a width, and a side cross-sectional area defined by the width and a height, wherein the length is greater than or equal to the width, and wherein the plan cross-sectional area is greater than the side cross-sectional area.

The at least one inlet may be part of a dump diffuser. The at least one inlet may include a height that spans about 60% of a height of the piezoelectric material. A base of the at least one inlet may be located along a base of the piezoelectric material. The dump diffuser may include at least one inlet flow port at an upper end of a plenum, and a flow outlet at a lower end of the plenum, the flow outlet being of a shape that provides a flow direction normal to an axial direction of the multi-dimensional acoustic standing wave generated by the at least one ultrasonic transducer.

Generally, the dump diffuser is used to make the incoming flow more uniform by reducing non-uniformities in the acoustic chamber resulting from gravity forces, so that the efficiency of the acoustophoretic device is maximized. The at least one inlet can be configured to permit ingress of fluid into the acoustic chamber at a flow rate of at least 800 milliliters per minute, and the fluid collector can be configured to permit egress of fluid out of the acoustic chamber at a flow rate of at least 25 milliliters per minute.

In some embodiments, the at least one inlet includes a first inlet at the first end of the acoustic chamber and a second inlet at a second end of the acoustic chamber opposite the first end thereof, such that inflow of fluid into the acoustic chamber is uniform and symmetrical.

Some embodiments of the acoustophoretic device further comprise a first angled wall below the at least one inlet and leading to the at least one concentrate outlet, wherein the first angled wall includes an angle from about 11° to about 60° relative to a first horizontal plane.

The at least one transducer may be a plurality of transducers spanning the length of the acoustic chamber. The plurality of transducers can be serially arranged in a single row. In some embodiments, the plurality of transducers includes a first row containing at least two transducers located above a second row containing at least two transducers. The at least one concentrate outlet may include a plurality of concentrate outlets.

The acoustic chamber may include a volume of at least 40 cubic inches.

In various embodiments of the acoustophoretic device, an angled roof, a parabolically curved roof, or a hypocycloidally curved roof leads from the first end and a second end of the acoustic chamber to the at least one fluid outlet. In other embodiments, the at least one fluid outlet is connected to a central area of the acoustic chamber.

The multi-dimensional acoustic standing wave may include an axial force component and a lateral force component which are of the same order of magnitude.

The ultrasonic transducer may comprise: a housing having a top end, a bottom end, and an interior volume; and a crystal at the bottom end of the housing having an exposed exterior surface and an interior surface, the crystal being able to generate acoustic waves when driven by a voltage signal. In some embodiments, a backing layer contacts the interior surface of the crystal, the backing layer being made of a substantially acoustically transparent material. The substantially acoustically transparent material can be balsa wood, cork, or foam. The substantially acoustically transparent material may have a thickness of up to 1 inch. The substantially acoustically transparent material can be in the form of a lattice. In other embodiments, an exterior surface of the crystal is covered by a wear surface material with a thickness of a half wavelength or less, the wear surface material being a urethane, epoxy, or silicone coating. The exterior surface of the crystal may also have wear surface formed from a matching layer or wear plate of material adhered to the exterior surface of the crystal. The matching layer or wear plate may be composed of aluminum oxide. In yet other embodiments, the crystal has no backing layer or wear layer, i.e. the crystal is free of a backing layer or a wear layer.

The multi-dimensional acoustic standing wave may be a three-dimensional standing wave.

Also disclosed in various embodiments are acoustophoretic devices, comprising: an acoustic chamber that includes at least one inlet at a first end thereof; at least one fluid outlet at a top end of the acoustophoretic device; at least one concentrate outlet at a bottom end of the acoustophoretic device; at least one ultrasonic transducer coupled to the acoustic chamber, the at least one ultrasonic transducer including a piezoelectric material configured to be driven by a voltage signal to create a multi-dimensional acoustic standing wave in the acoustic chamber; and a reflector across the acoustic chamber from the at least one ultrasonic transducer; wherein the at least one inlet is in the form of a dump diffuser that includes a flow outlet at a lower front end of a plenum, a first inlet flow port at an upper side end of the plenum, and a second inlet flow port at an upper rear end of the plenum.

Flow rates through the acoustic chamber can be from about 1 milliliter per minute to about 800 milliliters per minute. The devices of the present disclosure may be capable of separation efficiencies of 90% and more for cell concentrations from as low as 50,000 cells per milliliter of fluid to 80,000,000 cells per milliliter of fluid.

In particular embodiments, the multi-dimensional standing wave results in an acoustic radiation force having an axial force component and a lateral force component that are the same order of magnitude. In particular embodiments, the acoustic standing wave may be a multi-dimensional acoustic standing wave (e.g., a three-dimensional acoustic standing wave). Examples of such multi-dimensional acoustic standing waves can be found in commonly owned U.S. Pat. No. 9,228,183, the entire contents of which are hereby fully incorporated by reference.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 3A illustrates a roof whose flat exterior surface has a different angle from the flat interior surface. FIG. 3B illustrates a roof whose flat exterior surface has the same angle as the flat interior surface (i.e. a roof with constant thickness). FIG. 3C illustrates a roof with a hypocycloidally curved exterior and interior surface (i.e. the fluid path narrows very quickly). FIG. 3D illustrates a roof that forms a fluid path connecting to only a central area of the acoustic chamber.

FIGS. 4A-4D illustrate exemplary arrangements for acoustophoretic devices having one or more concentrate outlets. In devices with multiple concentrate outlets, the outlets are evenly spaced apart from each other. FIG. 4A illustrates a device with a base having one concentrate outlet. FIG. 4B illustrates a device with a base having one concentrate outlet. FIG. 4C illustrates a device with a base having three concentrate outlets. FIG. 4D illustrates a device with a base having four concentrate outlets.

FIGS. 5A-5C illustrate exemplary embodiments of a transducer assembly of an acoustophoretic device according to the present disclosure. FIG. 5A shows a piezoelectric transducer assembly including a total of six rectangular transducers arranged in two rows of three transducers. FIG. 5B shows a piezoelectric transducer assembly including a total of six square-shaped transducers arranged side-by-side in a single row. FIG. 5C shows a piezoelectric transducer assembly including a total of five rectangular transducers arranged in two rows, with the upper row including two transducers and the lower row including three transducers.

FIG. 7A and FIG. 7B illustrate more exemplary embodiments of a piezoelectric transducer assembly of an acoustophoretic device according to the present disclosure. FIG. 7A shows a piezoelectric transducer assembly including a total of three rectangular transducers arranged side-by-side in a single row. FIG. 7B shows a piezoelectric transducer assembly including a total of eight square-shaped transducers arranged side-by-side in a single row.

FIG. 28A illustrates the trapping line configurations for seven peak amplitudes of an ultrasonic transducer of the present disclosure. FIG. 28B is a perspective view illustrating a separator of the present disclosure. The fluid flow direction and the trapping lines are shown. FIG. 28C is a view from the fluid inlet along the fluid flow direction (arrow 814) of FIG. 28B, showing the trapping nodes of the standing wave where particles would be captured. FIG. 28D is a view taken through the transducers face at the trapping line configurations, along arrow 816 as shown in FIG. 28B.

DETAILED DESCRIPTION

Figure 1:
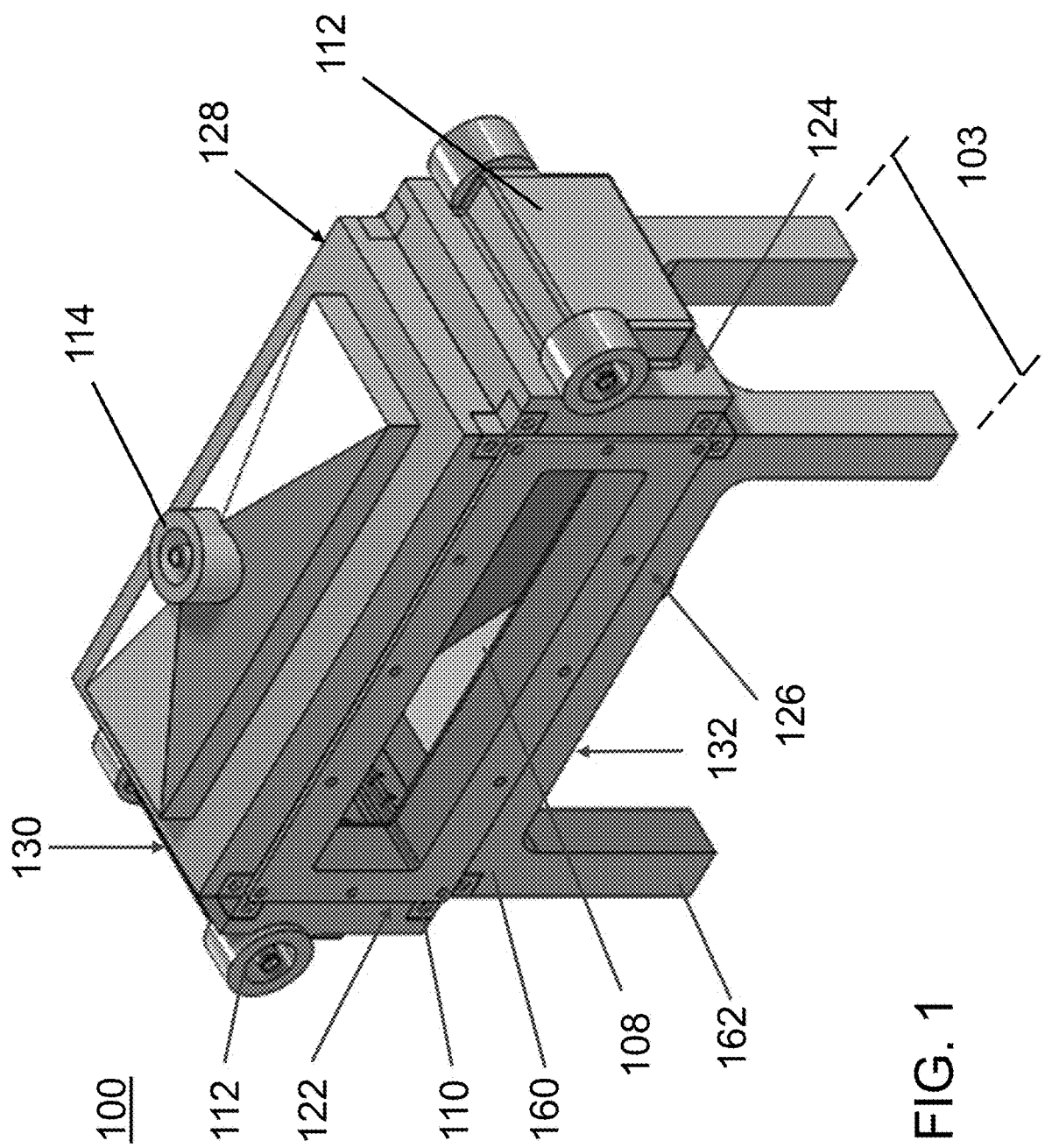
FIG. 1 is an exterior perspective view of a first exemplary acoustophoretic device according to the present disclosure. The device has an acoustic chamber whose horizontal cross-sectional area is greater than its vertical cross-sectional area.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" are used to refer to surfaces where the top is always higher than the bottom relative to an absolute reference, i.e. the surface of the earth. The terms "upwards" and "downwards" are also relative to an absolute reference; upwards is always against the gravity of the earth.

The term "parallel" should be construed in its lay sense of two surfaces that maintain a generally constant distance between them, and not in the strict mathematical sense that such surfaces will never intersect when extended to infinity.

The present application refers to "the same order of magnitude." Two numbers are of the same order of magnitude if the quotient of the larger number divided by the smaller number is a value of at least 1 and less than 10.

The term "virus" refers to an infectious agent that can only replicate inside another living cell, and otherwise exists in the form of a virion formed from a capsid that surrounds and contains DNA or RNA, and in some cases a lipid envelope surrounding the capsid.

The term "crystal" refers to a single crystal or polycrystalline material that is used as a piezoelectric material.

Acoustophoresis is a low-power, no-pressure-drop, no-clog, solid-state approach to particle removal from fluid dispersions: i.e., it is used to achieve separations that are more typically performed with porous filters, but it has none of the disadvantages of filters. In particular, the acoustophoretic devices of the present disclosure are suitable for use with bioreactors and operate at the macro-scale for separations in flowing systems with high flow rates. The acoustophoretic devices are designed to create a high intensity multi-dimensional ultrasonic standing wave that results in an acoustic radiation force that is larger than the combined effects of fluid drag and buoyancy or gravity, and is therefore able to trap (i.e., hold stationary) the suspended phase (i.e. cells) to allow more time for the acoustic wave to increase particle concentration, agglomeration and/or coalescence. This is an important distinction from previous approaches where particle trajectories were merely altered by the effect of the acoustic radiation force. As a result, in the present devices, the radiation force acts as a filter that prevents targeted particles (e.g., biological cells) from crossing the plane of the standing wave. The trapping capability of a standing wave may be varied as desired, for example by varying the flow rate of the fluid, the acoustic radiation force, and the shape of the acoustophoretic device to maximize cell retention through trapping and settling. This technology offers a green and sustainable alternative for separation of secondary phases with a significant reduction in cost of energy. Excellent particle separation efficiencies have been demonstrated for particle sizes as small as one micron. The acoustophoretic devices of the present disclosure have the ability to create ultrasonic standing wave fields that can trap particles in flow fields with flow rates greater than 1 mL/minute.

The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy/gravitational force, the particle is trapped within the acoustic standing wave field. The action of the acoustic forces (i.e., the lateral and axial acoustic forces) on the trapped particles results in formation of tightly-packed clusters through concentration, clustering, clumping, agglomeration and/or coalescence of particles that, when reaching a critical size, settle continuously through enhanced gravity for particles heavier than the host fluid or rise out through enhanced buoyancy for particles lighter than the host fluid. Additionally, secondary inter-particle forces, such as Bjerkness forces, aid in particle agglomeration.

Most biological cell types present a higher density and lower compressibility than the medium in which they are suspended, so that the acoustic contrast factor between the cells and the medium has a positive value. As a result, the axial acoustic radiation force (ARF) drives the cells towards the standing wave pressure nodes. The axial component of the acoustic radiation force drives the cells, with a positive contrast factor, to the pressure nodal planes, whereas cells or other particles with a negative contrast factor are driven to the pressure anti-nodal planes. The radial or lateral component of the acoustic radiation force is the force that traps the cells. The radial or lateral component of the ARF is larger than the combined effect of fluid drag force and gravitational force. For small cells or emulsions the drag force $F_D$ can be expressed as:

$$\vec{F}_D = 4\pi \mu_f R_p (\vec{U}_f - \vec{U}_p) \left[ \frac{1 + \frac{3}{2}\hat{\mu}}{1 + \hat{\mu}} \right]$$

where $U_f$ and $U_p$ are the fluid and cell velocity, $R_p$ is the particle radius, $\mu_f$ and $\mu_p$ are the dynamic viscosity of the fluid and the cells, and $\hat{\mu}=\mu_p/\mu_f$ is the ratio of dynamic viscosities. The buoyancy force $F_B$ is expressed as:

$$F_B = \tfrac{4}{3}\pi R_p^3 (\rho_f - \rho_p).$$

For a cell to be trapped in the multi-dimensional ultrasonic standing wave, the force balance or sum of the force vectors on the cell may be assumed to be zero, and therefore an expression for lateral acoustic radiation force $F_{LRF}$ can be found, which is given by:

$$F_{LRF} = F_D + F_B.$$

For a cell of known size and material property, and for a given flow rate, this equation can be used to estimate the magnitude of the lateral acoustic radiation force.

One theoretical model that is used to calculate the acoustic radiation force is based on the formulation developed by Gor'kov. The primary acoustic radiation force $F_A$ is defined as a function of a field potential U, $F_A = -\nabla(U)$, where the field potential U is defined as $$U = V_0 \left[ \frac{\langle p^2 \rangle}{2\rho_f c_f^2} f_1 - \frac{3\rho_f \langle u^2 \rangle}{4} f_2 \right],$$

and $f_1$ and $f_2$ are the monopole and dipole contributions defined by $$f_1 = 1 - \frac{1}{\Lambda \sigma^2}, \quad f_2 = \frac{2(\Lambda - 1)}{2\Lambda + 1},$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and $<>$ indicates time averaging over the period of the wave.

Gork'ov's model is for a single particle in a standing wave and is limited to particle sizes that are small with respect to the wavelength of the sound fields in the fluid and the particle. It also does not take into account the effect of viscosity of the fluid and the particle on the radiation force. As a result, this model cannot be used for the macro-scale ultrasonic separators discussed herein since particle clusters can grow quite large. A more complex and complete model for acoustic radiation forces that is not limited by particle size was therefore used. The models that were implemented are based on the theoretical work of Yurii Ilinskii and Evgenia Zabolotskaya as described in AIP Conference Proceedings, Vol. 1474-1, pp. 255-258 (2012). These models also include the effect of fluid and particle viscosity, and therefore are a more accurate calculation of the acoustic radiation force. Additional in-house models have been developed to calculate acoustic trapping forces for cylindrical shaped objects, such as the "hockey pucks" of trapped particles in the standing wave, which closely resemble a cylinder.

The lateral force of the total acoustic radiation force (ARF) generated by the ultrasonic transducers of the present disclosure is significant and is sufficient to overcome the fluid drag force. This lateral ARF can thus be used to retain cells within the acoustic standing wave while fluid flows past the standing wave. Additionally, as explained above, this action of the acoustic forces (i.e., lateral and axial acoustic forces) on the trapped particles results in formation of tightly packed clusters through concentration, agglomeration and/or coalescence of particles that settle through enhanced gravity (particles heavier than the host fluid) or buoyancy (particles lighter than the host fluid). Relatively large solids of one material can thus be separated from smaller particles of a different material, the same material, and/or the host fluid through enhanced gravitational separation.

The multi-dimensional standing wave generates acoustic radiation forces in both the axial direction (i.e., in the direction of the standing wave, between the transducer and the reflector, perpendicular to the flow direction) and the lateral direction (i.e., in the flow direction). As the mixture flows through the acoustic chamber, particles in suspension experience a strong axial force component in the direction of the standing wave. Since this acoustic force is perpendicular to the flow direction and the drag force, it quickly moves the particles to pressure nodal planes or anti-nodal planes, depending on the contrast factor of the particle. The lateral acoustic radiation force then acts to move the concentrated particles towards the center of each planar node, resulting in agglomeration or clumping. The lateral acoustic radiation force component overcomes fluid drag, which permits clumps of particles to continually grow and then drop out of the mixture due to gravity. A drop in drag per particle as the particle cluster increases in size and drop in acoustic radiation force per particle as the particle cluster grows in size, may be considered together or independently in the operation of the acoustic separator device. In at least some examples in the present disclosure, the lateral force component and the axial force component of the multi-dimensional acoustic standing wave are of the same order of magnitude. In this regard, it is noted that in a multi-dimensional acoustic standing wave, the axial force may have a different value than the lateral force, e.g. be weaker or stronger, or may be equal or equivalent, but the lateral force of a multi-dimensional acoustic standing wave is greater than the lateral force of a planar standing wave, sometimes by two orders of magnitude or more.

An acoustophoretic filtering device can be used in at least two different ways. First, the standing waves can be used to trap expressed biomolecules (e.g. phytochemicals, recombinant proteins or monoclonal antibodies) and separate this desired product from the cells, cell debris, and media. The expressed biomolecules can then be diverted and collected for further processing. Second, the standing waves can be used to trap the cells and cell debris present in the cell culture media. The cells and cell debris, having a positive contrast factor, move to the nodes (as opposed to the anti-nodes) of the standing wave. As the cells and cell debris agglomerate at the nodes of the standing wave, there is also a physical scrubbing of the cell culture media that occurs whereby more cells are trapped as they come in contact with the cells that are already held within the standing wave. This generally separates the cells and cellular debris from the cell culture media. When the cells in the standing wave agglomerate to the extent where the mass is no longer able to be held by the acoustic wave, the aggregated cells and cellular debris that have been trapped can fall out of the fluid stream through gravity, and can be collected separately. To aid this gravitational settling of the cells and cell debris, the standing wave may be interrupted to allow all of the cells to fall out of the fluid stream that is being filtered. This process can be useful for dewatering. The expressed biomolecules may have been removed beforehand, or remain in the fluid stream (i.e. cell culture medium).

In the present disclosure, a perfusion bioreactor can also be used to generate cells that can subsequently be used for various applications, including cell therapy. In this type of process, the biological cells to be used in the cell therapy are cultured in the bioreactor and expanded (i.e. to increase the number of cells in the bioreactor through cell reproduction). These cells may be lymphocytes such as T cells (e.g., regulatory T-cells (Tregs), Jurkat T-cells), B cells, or NK cells; their precursors, such as peripheral blood mononuclear cells (PBMCs); and the like. In the perfusion bioreactor, the cell culture media (aka host fluid), containing some cells, is sent from the bioreactor to a filtering device that produces an acoustic standing wave. A majority of the cells are trapped and held in the acoustic standing wave, while the remaining host fluid and other cells in the host fluid are returned to the bioreactor. As the quantity of trapped cells increases, they form larger clusters that will fall out of the acoustic standing wave at a critical size due to gravity forces. The clusters can fall into a concentrate outlet outside a region of the acoustic standing wave, such as below the acoustic standing wave, from which the cells can be recovered for use in cell therapy. Only a small portion of the cells are trapped and removed from the bioreactor via the concentrate outlet, and the remainder continue to reproduce in the bioreactor, allowing for continuous production and recovery of the desired cells.

In these applications, the acoustophoretic devices of the present disclosure can act as a cell retention device. The systems described herein operate over a range of cell recirculation rates, efficiently retain cells over a range of perfusion (or media removal) rates, and can be tuned to fully retain or selectively pass some percentage of cells through fluid flow rate, transducer power or frequency manipulation. Power and flow rates can all be monitored and used as feedback in an automated control system.

The cells of interest may also be held in the flow chamber of the external filtering device through the use of an acoustic standing wave such that other moieties may be introduced in close proximity to and for the purpose of changing the target cells. Such an operation would include the trapping of T cells and the subsequent introduction of modified lentivirus materials with a specific gene splice such that the lentivirus with a specific gene splice will transfect the T cell and generate a chimeric antigen receptor T cell also known as a CAR-T cell.

The acoustic filtering devices of the present disclosure are designed to maintain a high intensity three-dimensional acoustic standing wave. The device is driven by a function generator and amplifier (not shown). The device performance is monitored and controlled by a computer. It may be desirable, at times, due to acoustic streaming, to modulate the frequency or voltage amplitude of the standing wave. This modulation may be done by amplitude modulation and/or by frequency modulation. The duty cycle of the propagation of the standing wave may also be utilized to achieve certain results for trapping of materials. In other words, the acoustic beam may be turned on and shut off at different frequencies to achieve desired results.

Figure 2:
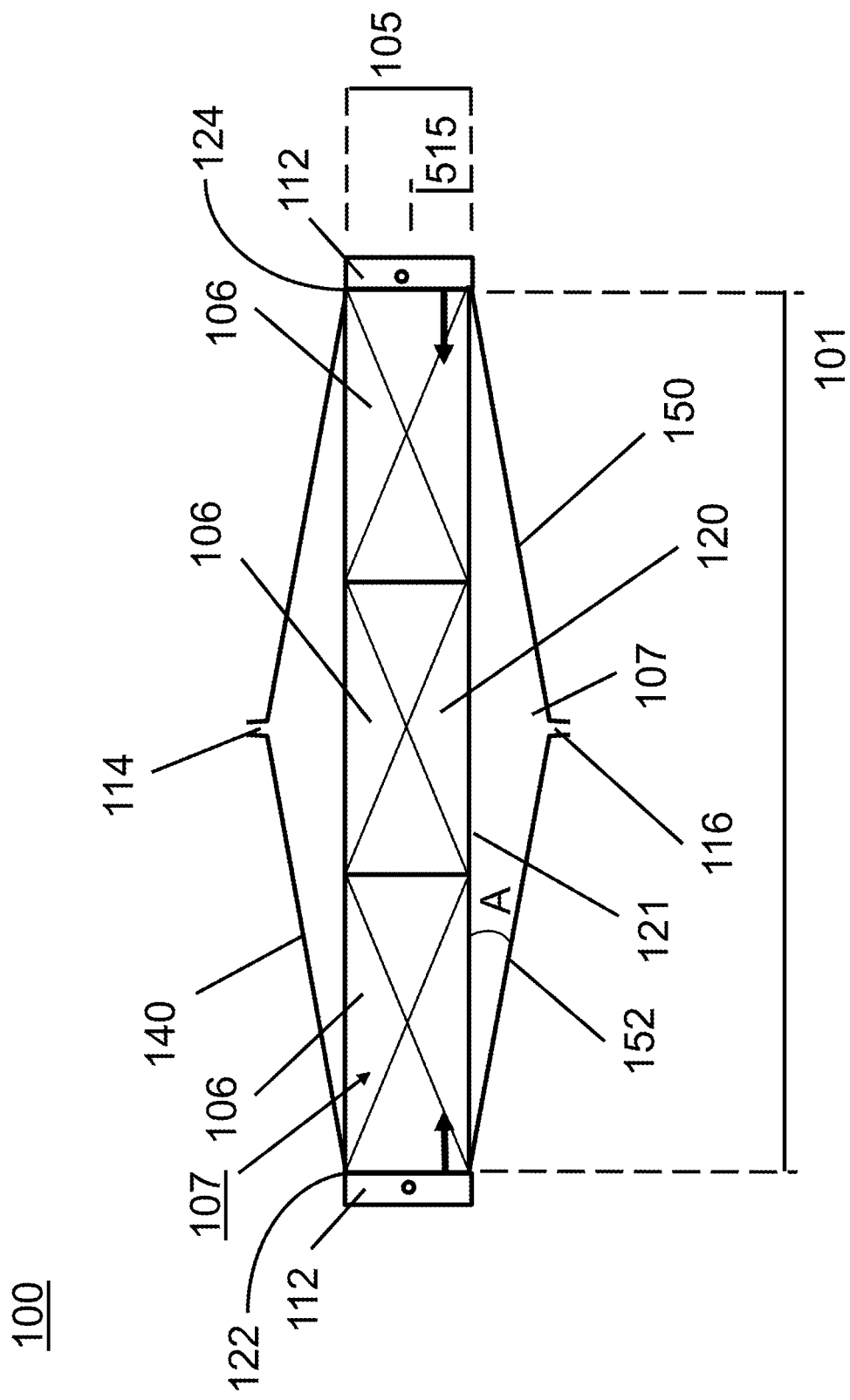
FIG. 2 is a cross-sectional view of the acoustophoretic device of FIG. 12.

The acoustophoretic devices of the present disclosure can handle higher flow rates and larger flow volumes compared to conventional devices. A first exemplary embodiment of an acoustophoretic device 100 for separating a primary/host fluid from a second fluid or particulate is illustrated in FIG. 1 and FIG. 2. FIG. 1 is an exterior perspective view, and FIG. 2 is a front cross-sectional view of the device. The design of the device provides a vertical plane or line of flow symmetry, so that a more uniform flow for the fluid through the device occurs.

Turning first to FIG. 1, the acoustophoretic device 100 is formed from a sidewall 110. As illustrated here, the sidewall 110 has a rectangular shape, so that the device has a first side end 122; a second side end 124 spaced apart from and opposite the first side end 122; a front side 126; a rear side 128 spaced apart from and opposite the front side 126; a top end 130; and a bottom end 132 that is spaced apart from and opposite the top end 130. Also illustrated here is a support frame 160 for the device. Legs 162 are shown extending from the support frame. The support frame can be integral with, or a separate structure from, the device 100.

Referring now to FIG. 2, a roof 140 is located on top of the sidewall 110, and a base 150 is located below the sidewall 110. Together, the sidewall 110, roof 140, and the base 150 enclose an interior volume 107. At least one concentrate outlet 116 is located at the bottom end of the device 100. As will be explained further herein, concentrated particulates will exit the interior volume 107 through the concentrate outlet(s). The base is illustrated as having two angled walls 152 that taper down to the concentrate outlet 116. It is noted that these walls 152 appear as straight lines due to the cross-sectional view—in three dimensions, the walls are conical.

At least one fluid inlet 112 is present at the first side end 122, which permits fluid to enter from the exterior of the device 100 into the interior volume 107. As illustrated here, two fluid inlets 112 are present, one on each of the side ends 122, 124. At least one fluid outlet 114 is present at the top end of the device 100. As will be explained further herein, fluid will exit the interior volume 107 through the fluid outlet(s). The fluid inlets 112 and fluid outlet 114 are also visible in FIG. 1.

Referring now to FIG. 1 and FIG. 2 together, at least one ultrasonic transducer 106 and at least one reflector 108 are located on opposite sides of the interior volume, and an acoustic chamber 120 is present between them. As illustrated here, three ultrasonic transducers 106 are located on the rear side 128 of the device, and the reflector(s) 108 are located on the front side 126 of the device.

It is noted that the volume of the acoustic chamber 120 and the interior volume 107 are not coextensive. The volume of the acoustic chamber is defined by the sidewall 110. In contrast, the interior volume 107 also includes volume from the roof 140 and the base 150. It is also noted that the angled walls 152 have an interior angle A measured relative to a horizontal plane (defined here by the bottom 121 of the acoustic), with the angle A being in embodiments from about 10° to about 60°, including about 30° to about 45°.

Referring still to FIG. 1 and FIG. 2 together, the acoustic chamber 120 has a length 101 between the first side end and the second side end; a width 103 between the front side and the rear side; and a height 105 that is defined by the height of the ultrasonic transducer(s). The length 101 and the width 103 thus define a plan cross-sectional area (i.e. a horizontal cross-sectional area), while the width 103 and the height 105 define a side cross-sectional area (i.e. a vertical cross-sectional area). As seen here, the plan cross-sectional area is greater than the side cross-sectional area.

In particular embodiments, the acoustic chamber 120 can have a volume of at least 40 cubic inches, such that large volumes of fluid can be processed within the acoustic chamber. In this regard, the fluid inlet(s) 112 of the device can be configured to permit the ingress of fluid into the acoustic chamber at a flow rate of at least 800 milliliters per minute (mL/min).

FIGS. 3A-3D are front views of four different roofs 140 that can be used in the acoustophoretic device. The roof forms a fluid path leading from the acoustic chamber 120 of the acoustophoretic device to the fluid outlet(s) 114 at the top of the device. In these figures, each roof 140 has an interior surface 142 and an exterior surface 144. It is noted that other roof shapes and configurations can also be used, as will be seen later herein. In particular embodiments, the fluid outlets can be configured to permit the egress of fluid out of the acoustic chamber at a flow rate of at least 25 mL/min.

Figure 3A:
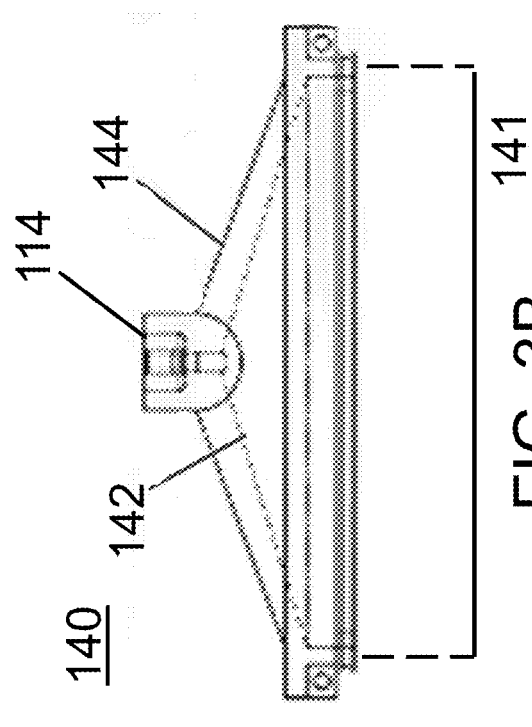
FIGS. 3A-3D illustrate four exemplary embodiments of roofs that form a fluid path leading from the acoustic chamber of the acoustophoretic device to the fluid outlet(s) at the top of the device.

FIG. 3A illustrates a roof 140 with a flat exterior surface 144 that has a different angle from the flat interior surface 142, such that the roof is thicker near the fluid outlet 114. The interior surface 142 extends from the fluid outlet 114 to a length 141 that is about the same as the length 101 of the acoustic chamber 107 of FIG. 2.

Figure 3B:
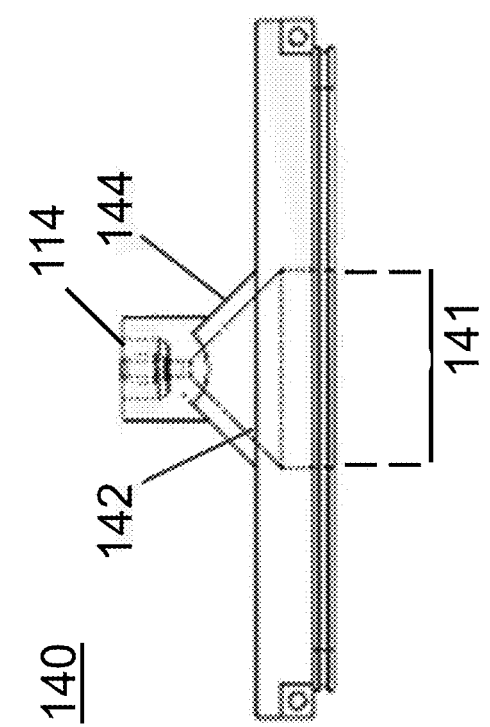

FIG. 3B illustrates a roof 140 whose flat exterior surface 144 has the same angle as the flat interior surface 142, i.e. the roof has a constant thickness. Again, the interior surface 142 extends from the fluid outlet 114 to a length 141 that is about the same as the length 101 of the acoustic chamber 107 of FIG. 2.

Figure 3C:
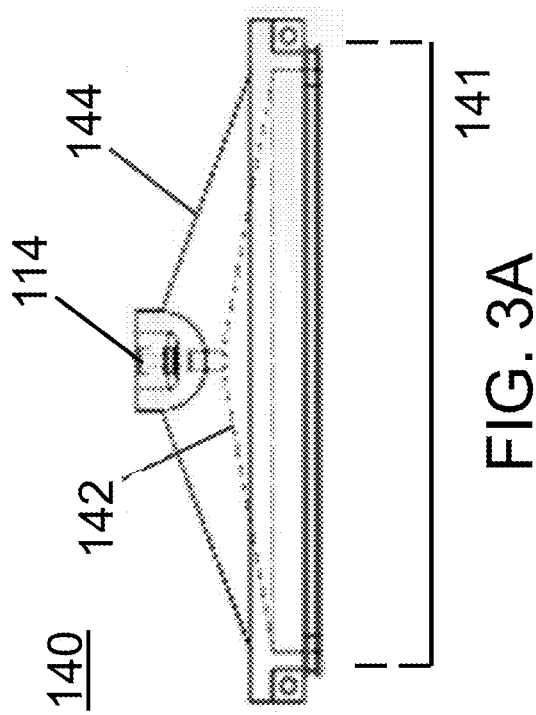

FIG. 3C illustrates a roof 140 having a hypocycloidally curved interior surface 142 and exterior surface 144. Again, the interior surface 142 extends from the fluid outlet 114 to a length 141 that is about the same as the length 101 of the acoustic chamber 107 of FIG. 2. The hypocycloidal shape of the interior surface causes the fluid path to narrow very quickly up to the fluid outlet 114.

Figure 3D:
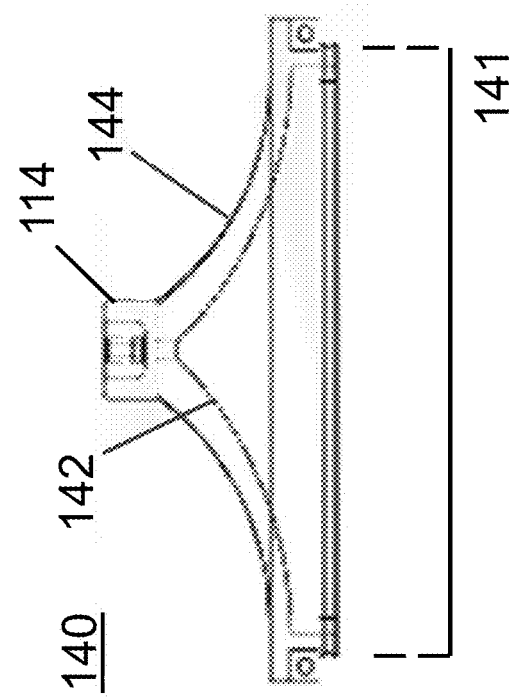

FIG. 3D illustrates a roof 140 with an interior surface 142 that extends to only a short length 141. In this embodiment, the length 141 is much shorter than the length 101 of the acoustic chamber, such that fluid only exits to the fluid outlet 114 from a central area of the acoustic chamber.

FIGS. 4A-4D are front views of four different bases 150 that can be used in the acoustophoretic device. The base forms a fluid path leading from the acoustic chamber 120 of the acoustophoretic device to the concentrate outlet(s) 116 at the bottom of the device. It is noted that other shapes and configurations can also be used for the base, as will be seen later herein. Legs 162 are also seen here, though again they do not need to be integral with the base.

FIG. 4A illustrates a base having one concentrate outlet 116. Two angled walls 152 lead from the sides of the acoustic chamber to the concentrate outlet 116.

FIG. 4B also illustrates a base having one concentrate outlet 116. The angled walls 152 here are shallower than those in FIG. 4A.

FIG. 4C illustrates a base having three concentrate outlets 116. The outlets 116 are spaced evenly apart from each other. Angled walls 152 lead to each concentrate outlet.

FIG. 4D illustrates a base having four concentrate outlets. The outlets 116 are spaced evenly apart from each other. Angled walls 152 lead to each concentrate outlet.

FIGS. 5A-5C show three different embodiments of a transducer assembly formed from a plurality of ultrasonic transducers, which can be used in the acoustophoretic devices of the present disclosure. A plurality of transducers allows for greater particle capture efficiency, especially when the transducers have different resonance frequencies, so that a larger range of particle (e.g. cell) sizes is captured. These transducer assemblies 170 are oriented along the length of the acoustic chamber, and the side ends 122, 124 and the top end 130 are labeled in each figure for orientation of the assembly.

FIG. 5A shows a piezoelectric transducer assembly 170 including a total of six rectangular transducers 106 arranged in two rows 172, 174 of three transducers. It is contemplated that in this arrangement the transducers collectively span the entire width and height of the acoustic chamber.

FIG. 5B shows a piezoelectric transducer assembly 170 including a total of six square-shaped transducers 106 arranged side-by-side in a single row 172. The transducers collectively span the entire width of the transducer assembly, but not the entire height of the transducer assembly.

Figure 6:
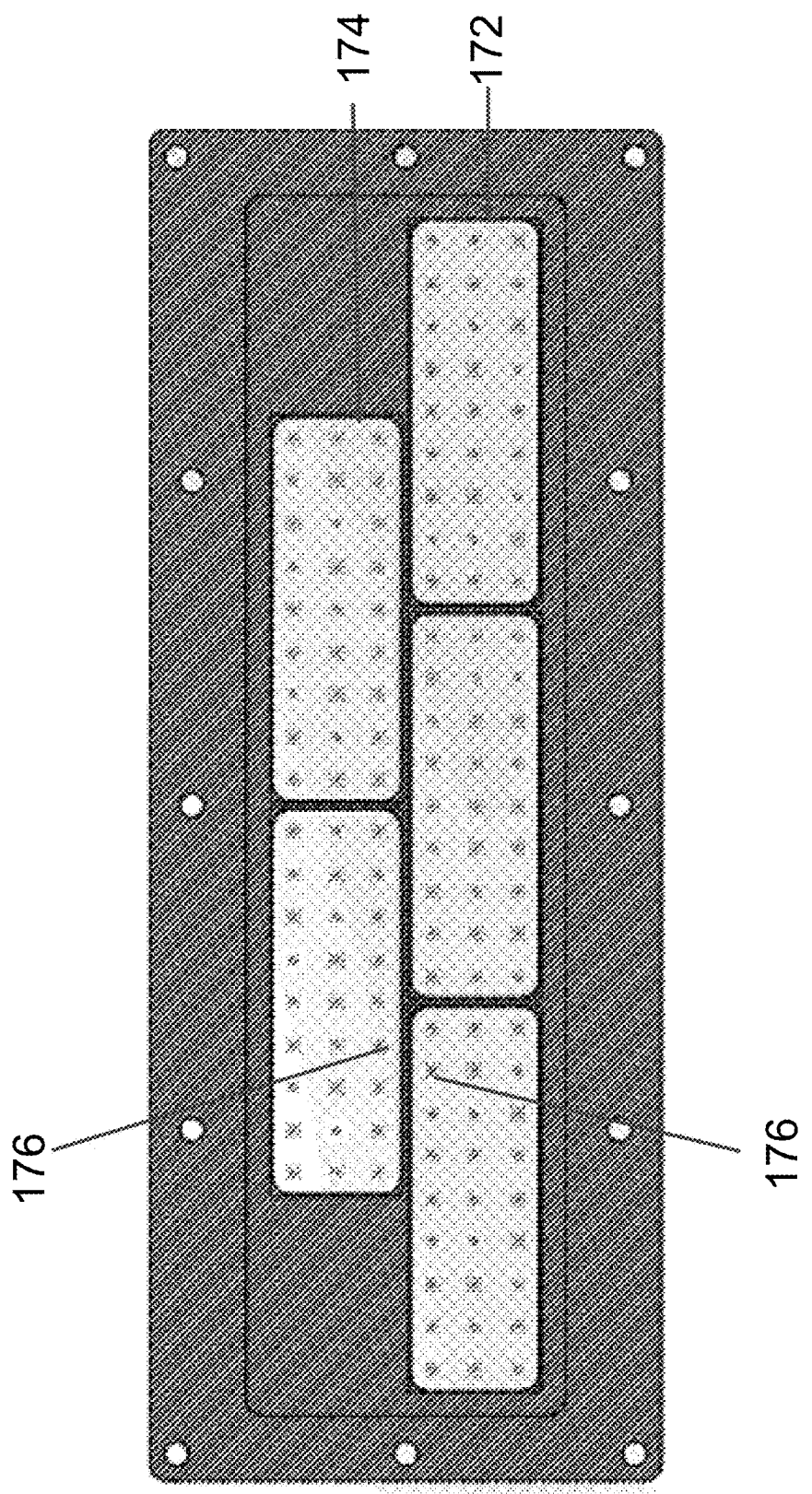
FIG. 6 illustrates a simulation of particle clusters being trapped by acoustic standing waves generated by the transducers of the transducer assembly of FIG. 5C.

FIG. 5C shows a piezoelectric transducer assembly 170 including a total of five rectangular transducers 106 arranged in two rows, with the upper row 174 including two transducers and the lower row 172 including three transducers. It is noted that the transducers in the upper row 174 are staggered/offset with respect to the transducers in the lower row 172. One benefit of this arrangement is illustrated in FIG. 6, which indicates the location of multi-dimensional acoustic standing waves 176 that will be generated by the transducers. As can be seen here, the staggering of the transducers causes the acoustic standing waves 176 to also be staggered, so that the standing waves generated by the upper row 174 are staggered from the standing waves in the lower row 172. As previously explained, particles/cells that are trapped in the multi-dimensional acoustic standing waves will agglomerate and form clusters that eventually fall out of the standing waves and travel downwards towards the concentrate outlet. This staggering permits the clusters that fall downwards from the upper row 174 to avoid passing through the acoustic standing waves generated in the lower row 172, so that the clusters being formed in the lower row 172 are not disturbed or disrupted.

It is also contemplated that the plurality of transducers can be arranged serially in a single row, such as in FIG. 7A and FIG. 7B. FIG. 7A shows a transducer assembly 170 including a total of three rectangular transducers 106 arranged side-by-side in a single row. FIG. 7B shows a transducer assembly 170 with a total of eight square-shaped transducers 106 arranged side-by-side in a single row.

Referring now back to FIG. 1 and FIG. 2, the device 100 has symmetrical fluid inlets 112 placed on opposite sides of the acoustic chamber. In particular embodiments, these inlets are in the form of dump diffusers, which provide a more uniform flow of the mixture of host fluid and particulate into the acoustic chamber.

Briefly, each dump diffuser includes an entrance port through which the mixture of host fluid/second fluid or particulate flows into a hollow chamber. The mixture fills up the chamber in the dump diffuser, which reduces/eliminates flow pulsations and flow non-uniformities that result from pumps, hosing and horizontal inlet flow where gravity effects dominate. The mixture then flows horizontally out of the dump diffuser and enters the acoustic chamber 107. The dump diffuser brings the heavier mixture into the acoustic chamber (dark arrows) above the bottom of the chamber and below the ultrasonic transducer(s) 106 and the nodal clusters that form in the acoustic standing waves. This minimizes any disturbances of the clusters set up by inflowing material.

Figure 8:
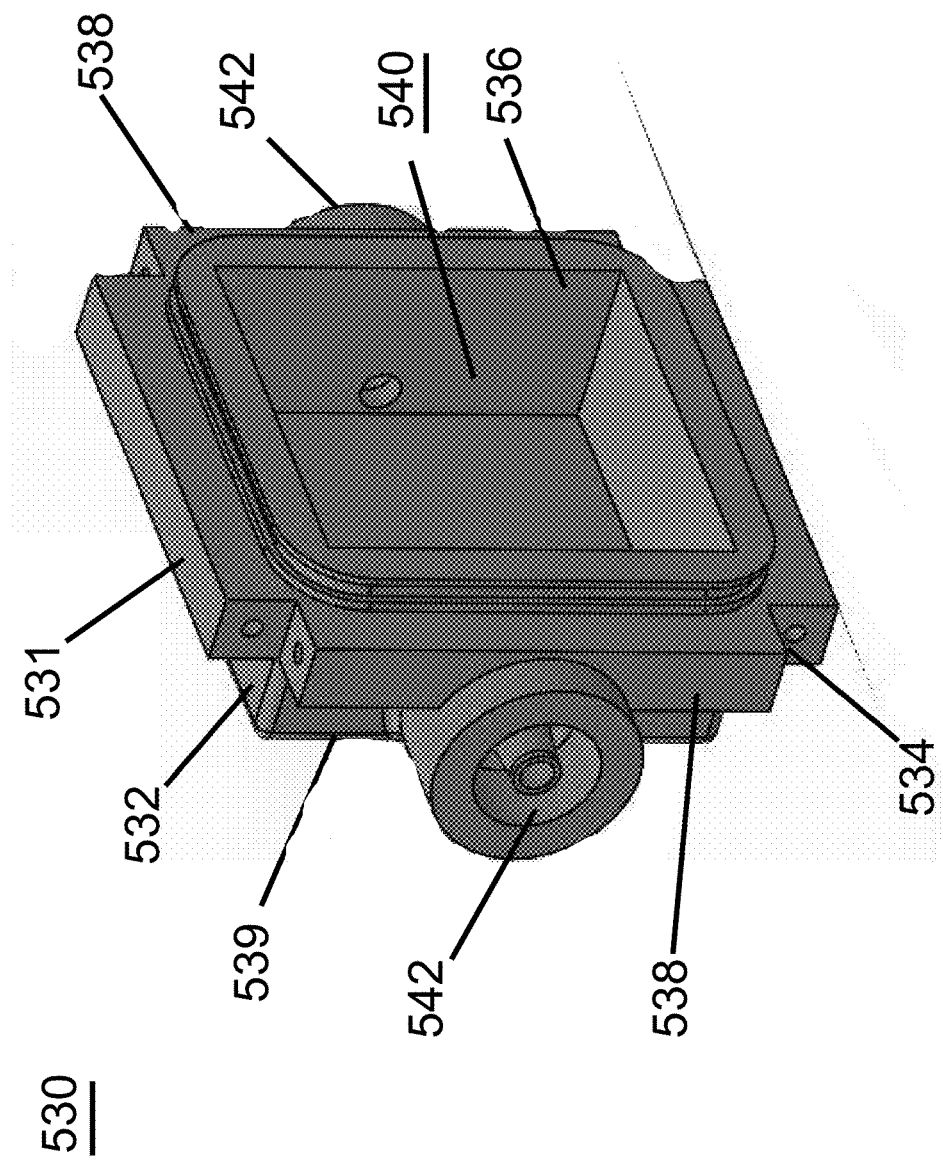
FIG. 8 is a perspective view of an exemplary dump diffuser.
Figure 9:
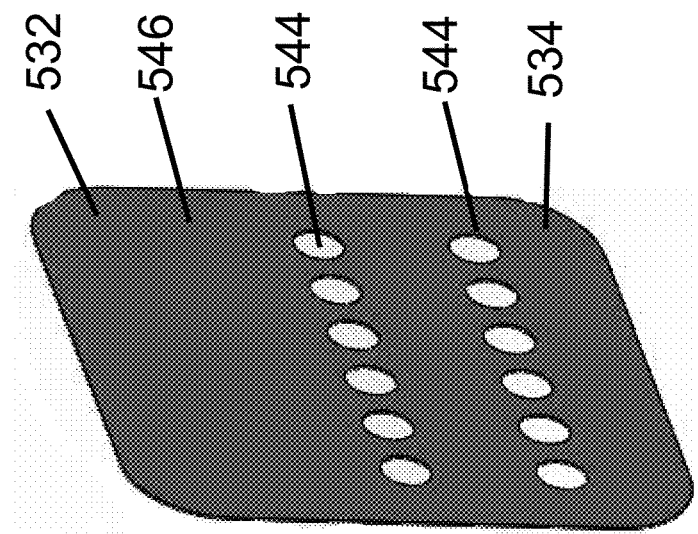
FIG. 9 is a side view of the exemplary dump diffuser of FIG. 10.

The structure and operation of the dump diffuser is illustrated in FIG. 8 and FIG. 9. FIG. 8 is a perspective view of the dump diffuser 530 with the front plate removed, showing both the interior and the exterior of a dump diffuser. FIG. 9 is a perspective view of the front plate of the dump diffuser.

Starting with FIG. 8, the dump diffuser 530 includes a housing 531 having an upper end 532, an opposite lower end 534, two side faces 538, a front face 536, and a rear face 539. A hollow chamber 540 is present within the housing 531. The dump diffuser also includes an entrance port 542 that receives the mixture and leads into the chamber 540. The entrance port 542 is present on the upper end and on a side face 538 of the housing; two entrance ports are visible here. FIG. 9 is a picture of the front plate 546 which is attached to the front face 536 of the housing. As illustrated here, the diffuser outlet(s) 544 is located on the lower end 534 and is in the form of two lines of holes, though these could also be in the form of a thin slot.

Referring now to both FIG. 2 and FIG. 8, in use, the mixture of host fluid/second fluid or particulate enters the dump diffuser 530 through entrance ports 542 and fills up the chamber 540. Pressure then pushes the mixture uniformly out through diffuser outlets 544. These diffuser outlets 544 also pass through the sidewall 110 of the device 100, and can also be considered as the fluid inlet 112 into the interior volume 107. The diffuser outlet(s) are placed above the bottom 121 of the acoustic chamber. In embodiments, the diffuser outlets are located above the chamber bottom 121 at a height 515 that is between 0% and 100% of the height 105 of the acoustic chamber, and more particularly between 5% and 25% of the height of the acoustic chamber. The diffuser outlets 544 provide a flow direction parallel to the axial direction of the acoustic standing waves generated by the ultrasonic transducer. The diffuser outlets are also arranged so that they are in opposing locations, so that the horizontal velocity of the fluid will decrease to zero in the center of the acoustic chamber.

The flow streamlines through the acoustic chamber are desirably symmetrical, since this minimizes non-uniformities, eddy disturbances, circulation, and disturbance of clusters falling down to concentrate outlet 116 to be collected. Symmetry also maximizes gravity forces in the inlet flow distribution and particle collection process. Because it is heavier than the permeate exiting at the top of the device, the (relatively) heavy incoming mixture comes in near the bottom of the acoustic chamber. The symmetrical inlets also assure that the incoming mixture spreads out across the bottom of the chamber due to gravity forces, and provides near uniform velocity profiles from bottom to top. The horizontal velocity of the mixture decreases towards and may equal zero as it approaches the center of the acoustic chamber due to the dual opposing inlet flows. In this example, a uniform velocity contributes to separation and collection results. The uniform velocity avoids peak velocities that might prevent the acoustic standing waves from overcoming particle drag that might impede the clusters from growing and continuously leaving the acoustic standing wave via gravity or buoyancy forces.

As the particle clusters drop out, the axial acoustic forces associated with the standing wave keep the clusters intact. This effect assures rapid dropping of the clusters with high terminal velocities, on the order of 1 cm/sec. This rate is extremely fast compared to the chamber flow velocities, which are on the order of 0.1 cm/sec to 0.3 cm/sec. The shallow wall angle of the base means the cylindrical particle clusters can drop a short distance before they exit the acoustic chamber, so that little dispersion of the clusters occurs. Ideally, the system operates with 3 to 12 trapping lines per square inch of transducer. The symmetry, minimum flow disturbance in the central collection region, and shallow collector walls provide good collection of the particles.

A second exemplary embodiment of an acoustophoretic device 600 is illustrated in FIGS. 10-12. FIG. 10 is a front cross-sectional view. FIG. 11 is an exterior perspective view of the front of the device. FIG. 12 is an exterior perspective view of the rear of the device. In this device, again, the plan cross-sectional area of the acoustic chamber is greater than the side cross-sectional area of the acoustic chamber.

Starting with FIG. 10, the acoustophoretic device 600 shares many similarities with device 100 of FIG. 1. Device 600 has a first side end 122 and a second opposite side end 124. A sidewall 110, roof 140 and a base 150 are present to define the interior volume 107. A dump diffuser 530 is present on each side end 122, 124, which acts as the fluid inlet 112 to the interior volume 107 of the device. Here, the roof 140 includes a parabolic interior surface 142 that leads to the fluid outlet 114 at the top end 130. Two concentrate outlets 116 are present in the base 152, with angled walls 152 leading to each outlet at the bottom end 132. Five ultrasonic transducers 106 are illustrated, with the rectangle indicating the piezoelectric material used to generate the multi-dimensional acoustic standing wave.

One notable aspect of the device that is more visible in FIG. 10 is the relationship of the placement of the dump diffuser 530/fluid inlet 112 to the ultrasonic transducers 106. As seen here, the fluid inlet 112 has a height 113 that is about 60% of the height 176 of the piezoelectric material. Also, the base 111 of the fluid inlet 112 is located along, i.e. aligned with, the base 177 of the piezoelectric material. In embodiments, the height of the fluid inlet can be from about 5% to about 75% of the height of the piezoelectric material.

Referring now to FIG. 11, the reflector 108 is visible on the front side 126 of the device 600. In addition, it can be seen that the fluid outlet 114 and the concentrate outlets 116 lead from the top/bottom ends of the interior volume to the rear side 128 of the device.

Also visible in FIG. 11 is an alternate construction for the dump diffuser 530. The dump diffuser of FIG. 8 has two inlet flow ports 542, both located on the side faces 538. In contrast, the dump diffuser of FIG. 8 has three inlet flow ports 542. Two of the inlet flow ports 542 are located on the side faces 538. The third inlet flow port 542 is located on the rear face 539 on the upper end 532 of the diffuser.

Referring now to FIG. 12, the ultrasonic transducer assembly 170 is seen. Five connectors 171 are visible, one for each of the transducers 106 visible in FIG. 10.

Experiments were performed using an acoustophoretic device of FIG. 1. The dimensions of the acoustic chamber were 9 inches by 3 inches by 2 inches (length by width by height). The device had six transducers arranged in two rows as illustrated in FIG. 5A. The experiments measured the percent reduction/clarification and packed cell mass (PCM) over time of an incoming water/yeast mixture.

In the graph of FIG. 13, the yeast mixture was 1.5% yeast and was flowed through the device at a flow rate of 810 mL/minute. The inlets of the device were not part of a dump diffuser (i.e. no front plate as illustrated in FIG. 9 was present). The ultrasonic transducers of the device were operated at 60 volts, 80 volts, and 100 volts. The devices were operated using acoustically transparent films (ATFs) and also without the use of any such ATFs. As can be seen in FIG. 28, the PCM (lower lines) was measured to be from about 20%-28% at 60 volts, from about 28%-35% at 80 volts, and from about 35%-38% at 100 volts, both with and without ATFs. The percent reduction/clarification of the mixture (upper lines) was about 75%-80% at 60 volts, from about 80%-90% at 80 volts, and from about 85%-90% at 100 volts, both with and without ATFs, though the devices seemed to have a slightly better separation/clarification efficiency without ATFs. Both the Percent Reduction and the PCM values suggested that operation at higher voltages resulted in better separation of water and yeast.

In the graph of FIG. 14, the yeast mixture was 3.0% yeast and was flowed through the device at a flow rate of 810 mL/minute. Again, the inlets of the device were not part of a dump diffuser. The ultrasonic transducers of the device were operated at 60 volts, 80 volts, and 100 volts. The devices were operated using five acoustically transparent films (ATFs). Here, the PCM (lower lines) was measured to be from about 18%-25% at 60 volts, from about 25%-29% at 80 volts, and from about 29%-30% at 100 volts. The percent reduction/clarification of the mixture (upper lines) was from about 55%-75% at 60 volts, from about 75%-82% at 80 volts, and from about 75%-82% at 100 volts.

Figure 15:
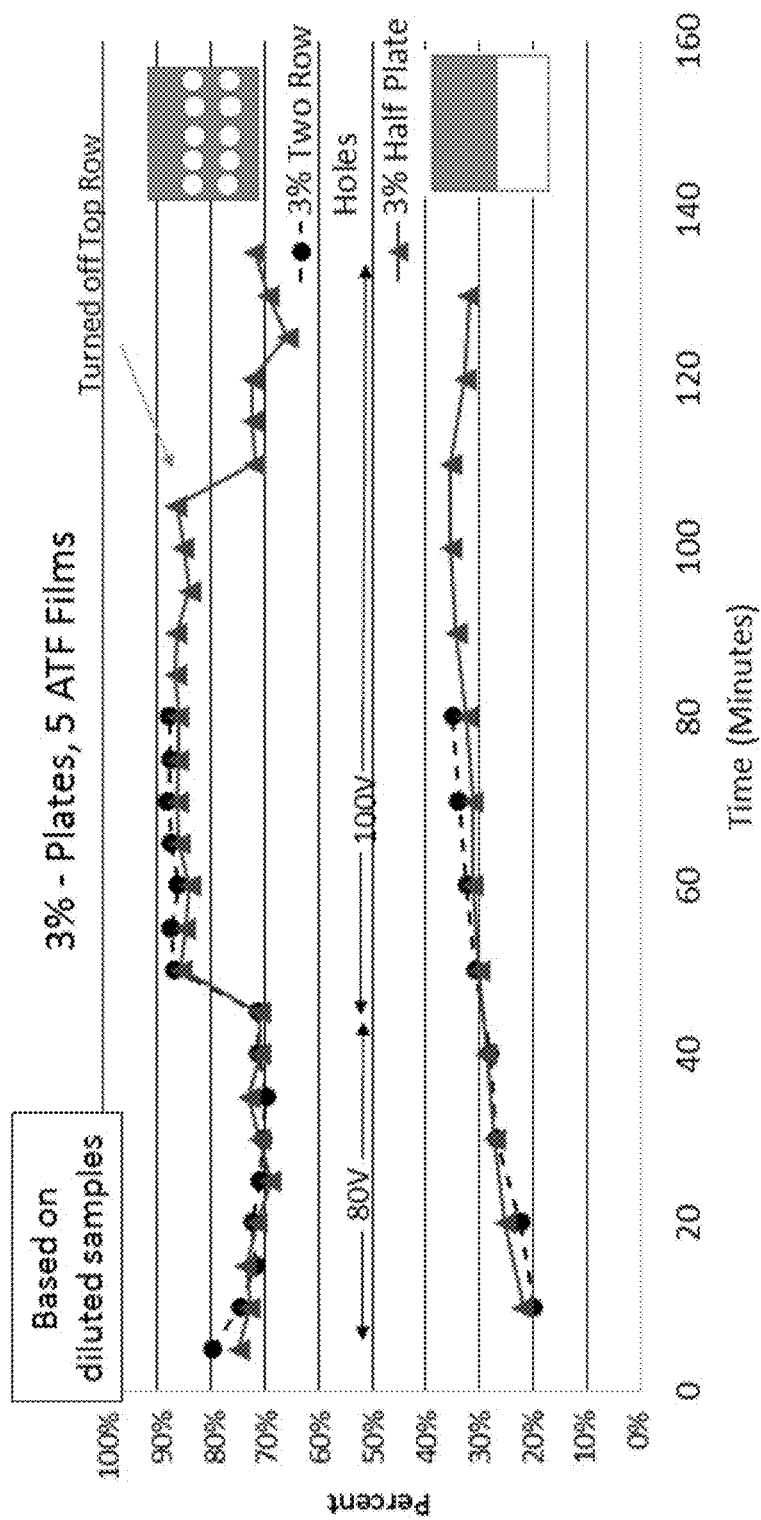
FIG. 15 is a graph showing the percent reduction/clarification over time of a 3% yeast mixture flowed at 810 mL/minute through a 9 inch by 3 inch by 2 inch (length by width by height) acoustophoretic device according to the present disclosure having five alternating tangential flow (ATF) films and operated at 80 volts and 100 volts. The lighter lines represent devices using a dump diffuser with two roles of holes according to the present disclosure, while the darker lines represent devices using a half-plate dump diffuser according to the present disclosure.

In the graph of FIG. 15, the yeast mixture was 3.0% yeast and was flowed through the device at a flow rate of 810 mL/minute. The inlets of the device were part of a dump diffuser with front plates. The darker lines represent a dump diffuser wherein the front plate was configured as a half plate (i.e. one large slot at the bottom of the front plate), and the lighter lines represent a dump diffuser where the front plate had two rows of holes. The ultrasonic transducers of the device were operated at 80 volts and 100 volts. The devices were operated using five ATFs. The PCM (lower lines) was measured to be from about 20%-30% at 80 volts and from about 30%-35% at 100 volts for the two-rows-holes front plate. The PCM for the half-plate front plate was about 20%-30% at 80 volts and from about 30%-35% at 100 volts. It is noted that the PCM for the half-plate front plate did not change significantly once the top row of ultrasonic transducers was turned off. The percent reduction/clarification of the mixture (upper lines) for the two-rows-holes front plate was about 68%-80% at 80 volts, and about 85%-90% at 100 volts with the top row turned on. The percent reduction/clarification of the mixture for the half-plate front plate was about 68%-80% at 80 volts, from about 85%-90% at 100 volts with the top row on, and then from about 65%-75% at 100 volts with the top row turned off.

Figure 16:
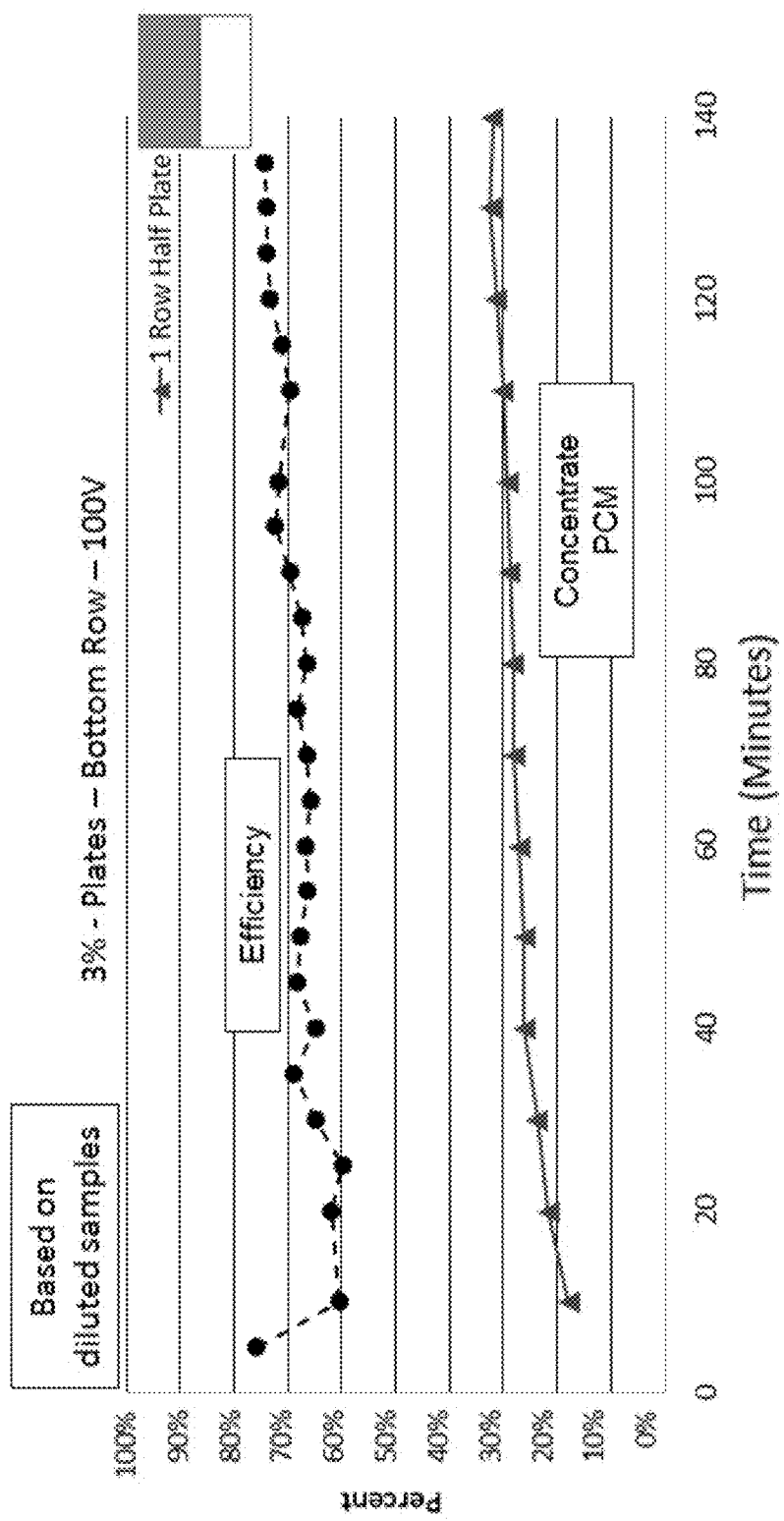
FIG. 16 is a graph showing the percent reduction/clarification (upper lines) and phase contrast microscopy (lower lines) over time of a 3% yeast mixture flowed at 810 mL/minute through a 9 inch by 3 inch by 2 inch (length by width by height) acoustophoretic device according to the present disclosure using a half-plate dump diffuser, five alternating tangential flow (ATF) films, and using a transducer assembly having two rows of transducers, where the top row is switched off and the bottom row is operated at 100 volts.

In the graph of FIG. 16, the yeast mixture was 3.0% yeast and was flowed through the device at a flow rate of 810 mL/minute. The inlets of the device were part of a dump diffuser, using a half-plate front plate. Only the bottom row of transducers was used, and the ultrasonic transducers of the device were operated at 100 volts. The PCM (lower line) was measured to be from about 18%-32%, and the percent reduction/clarification of the mixture (upper line) was about 60%-78%.

Figure 17:
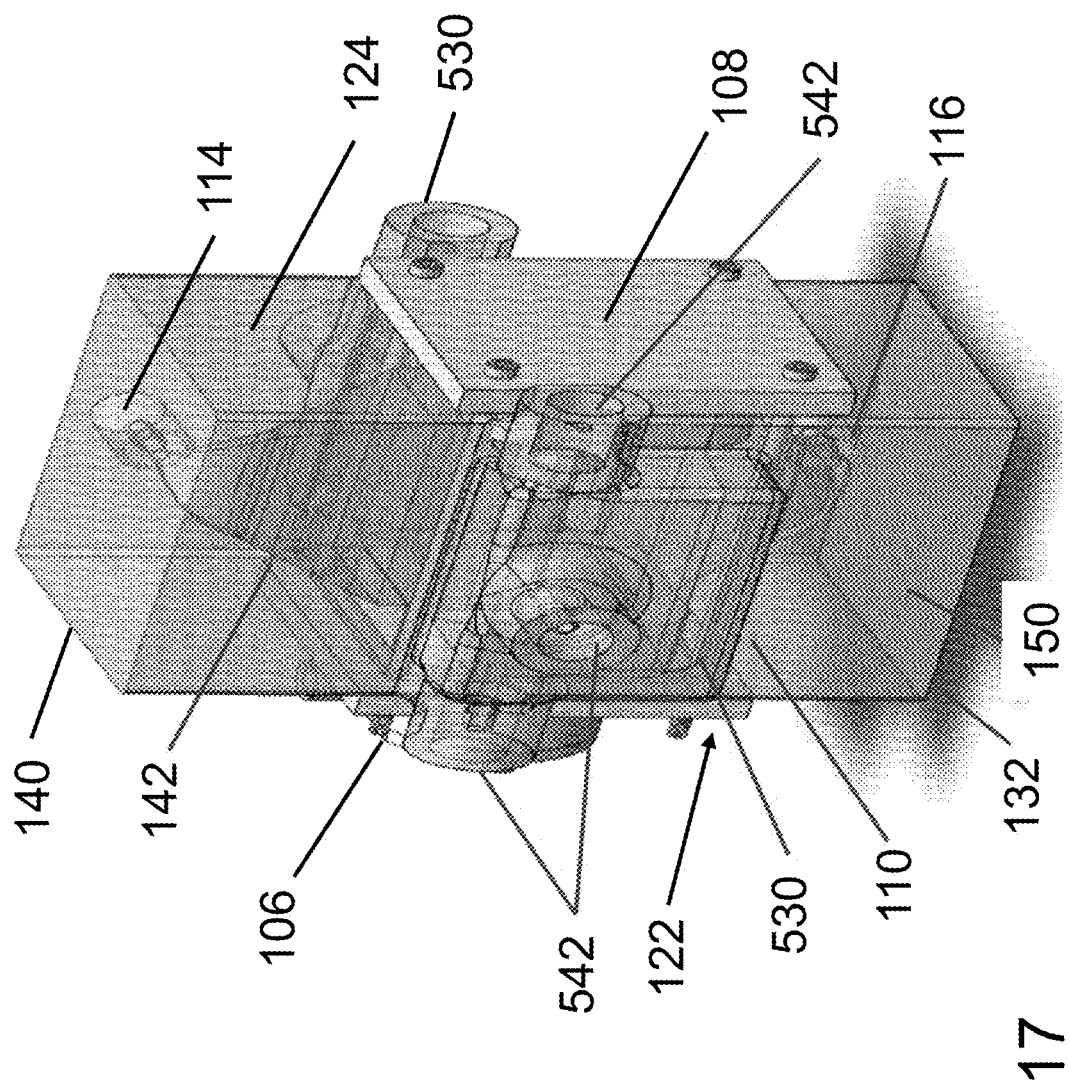
FIG. 17 is an exterior perspective view of a third exemplary acoustophoretic device according to the present disclosure. This embodiment notably uses a dump diffuser in which fluids enter the dump diffuser plenum along two different axes rather than only one axis (as in FIG. 1).
Figure 18:
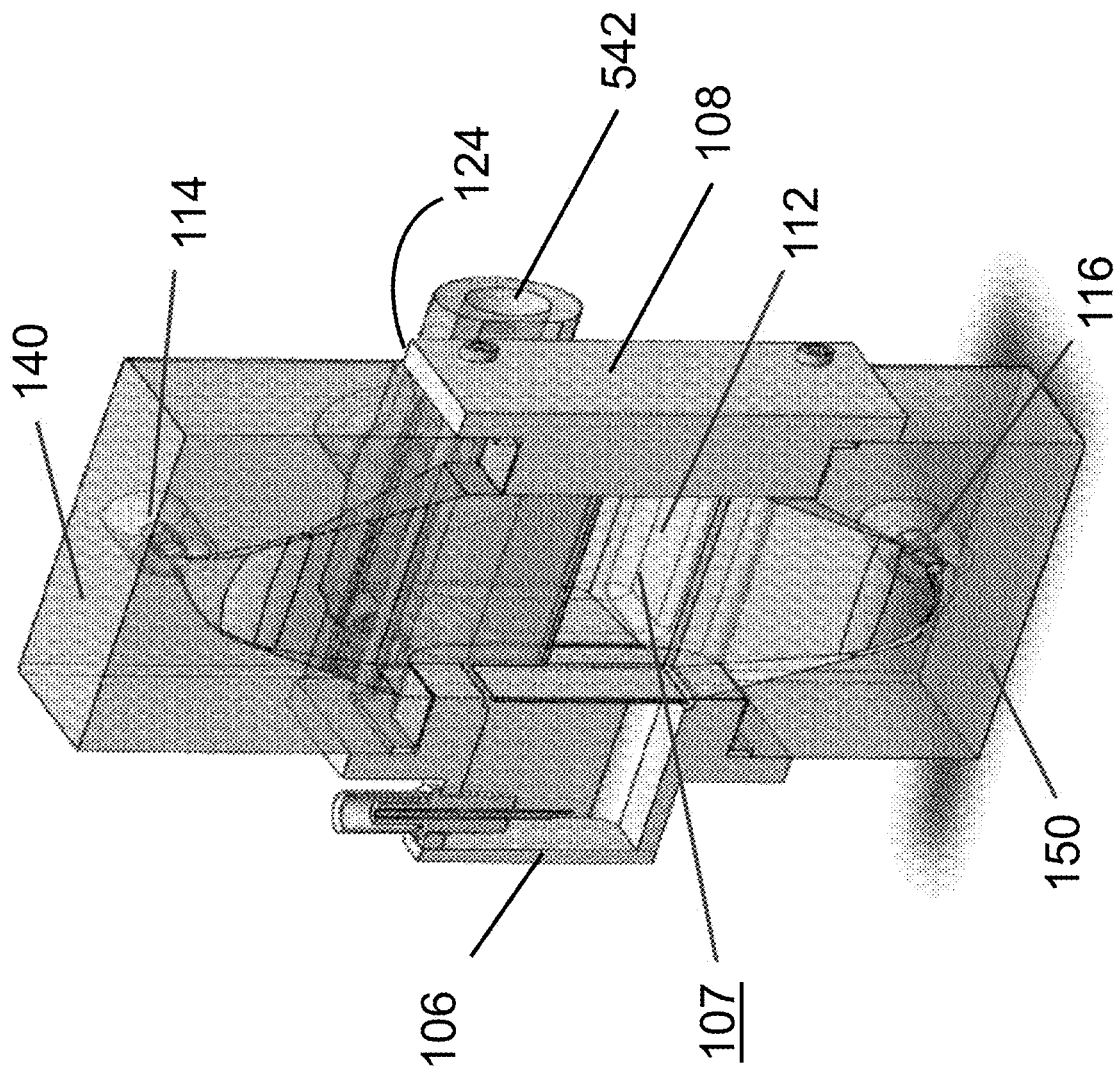
FIG. 18 is a perspective view of a side cross-section of the device of FIG. 17.
Figure 19:
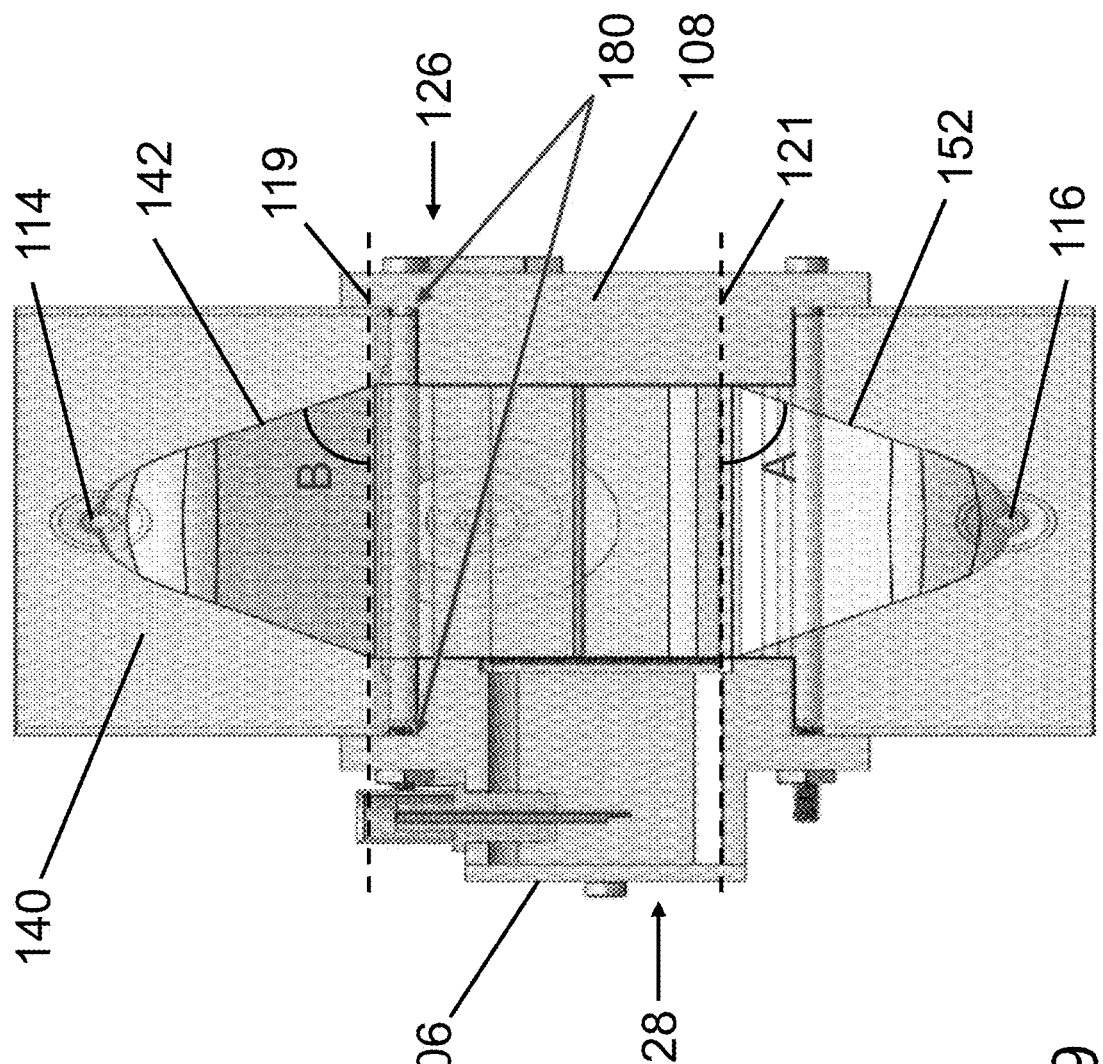
FIG. 19 is a side cross-sectional view of the acoustophoretic device of FIG. 19 showing additional aspects along with FIG. 18.
Figure 20:
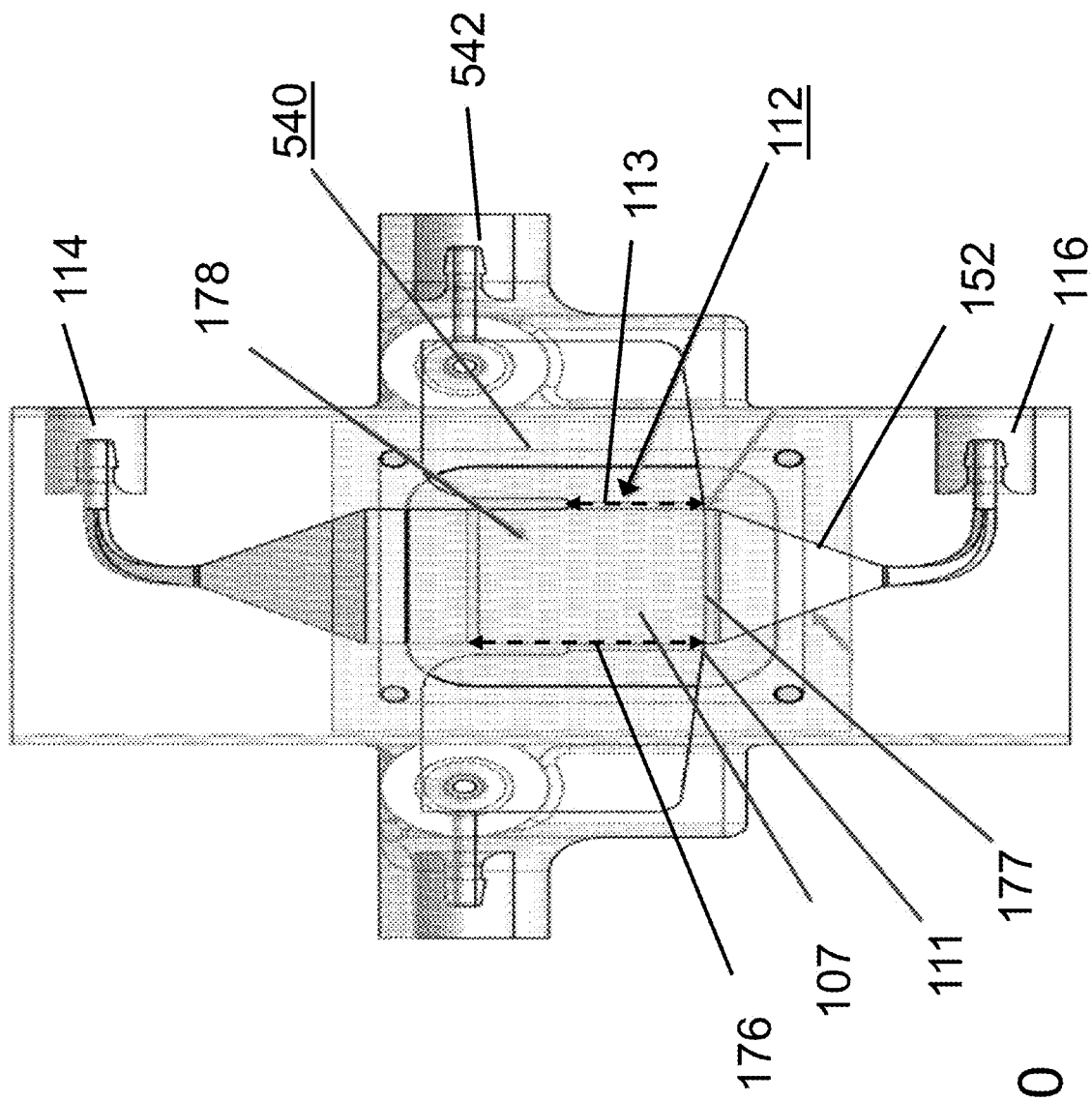
FIG. 20 is a front view of the acoustophoretic device of FIG. 17 with transparent walls to show additional features.
Figure 21:
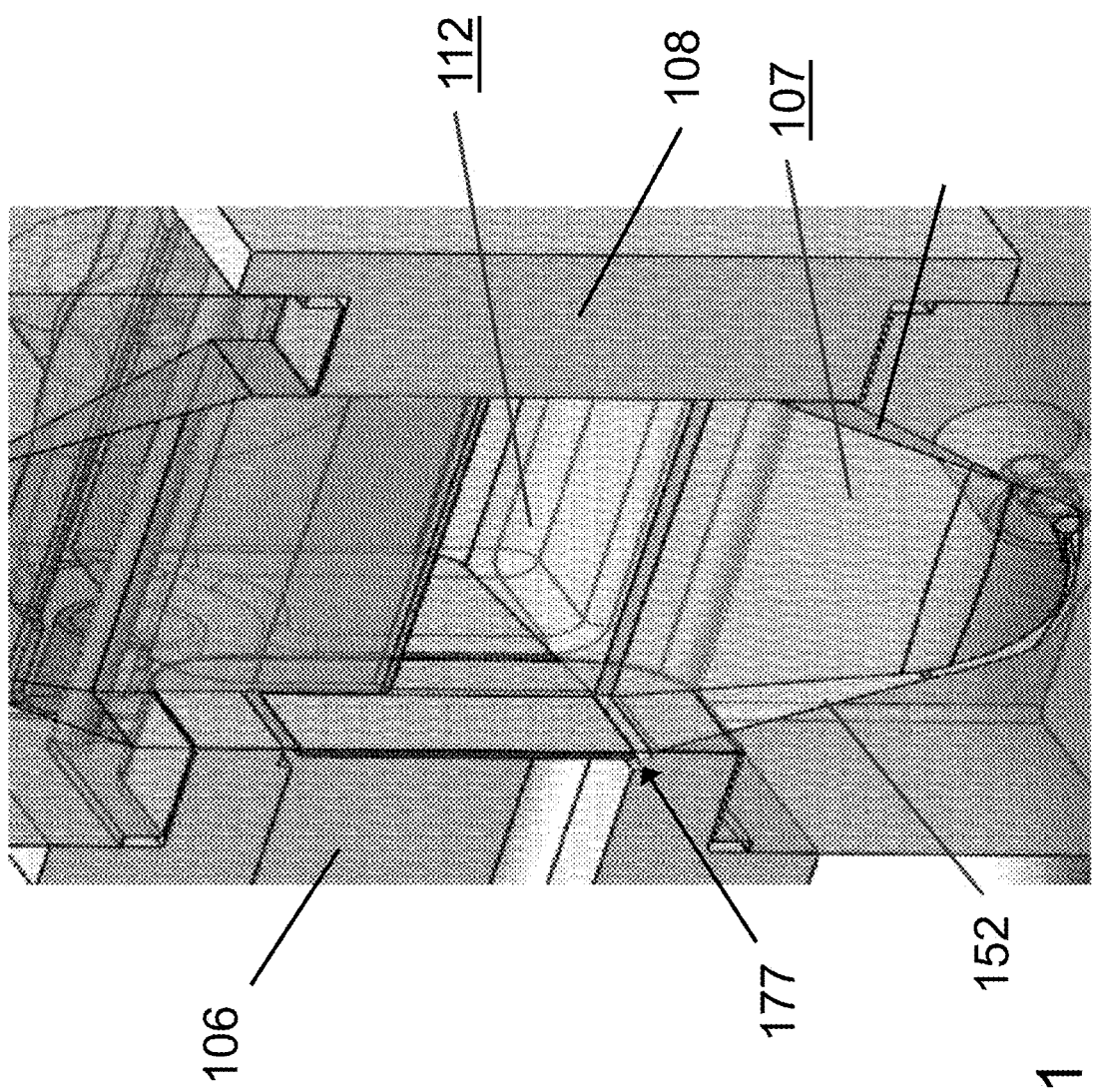
FIG. 21 is a magnified view of the flow chamber of the device of FIG. 17.
Figure 22:
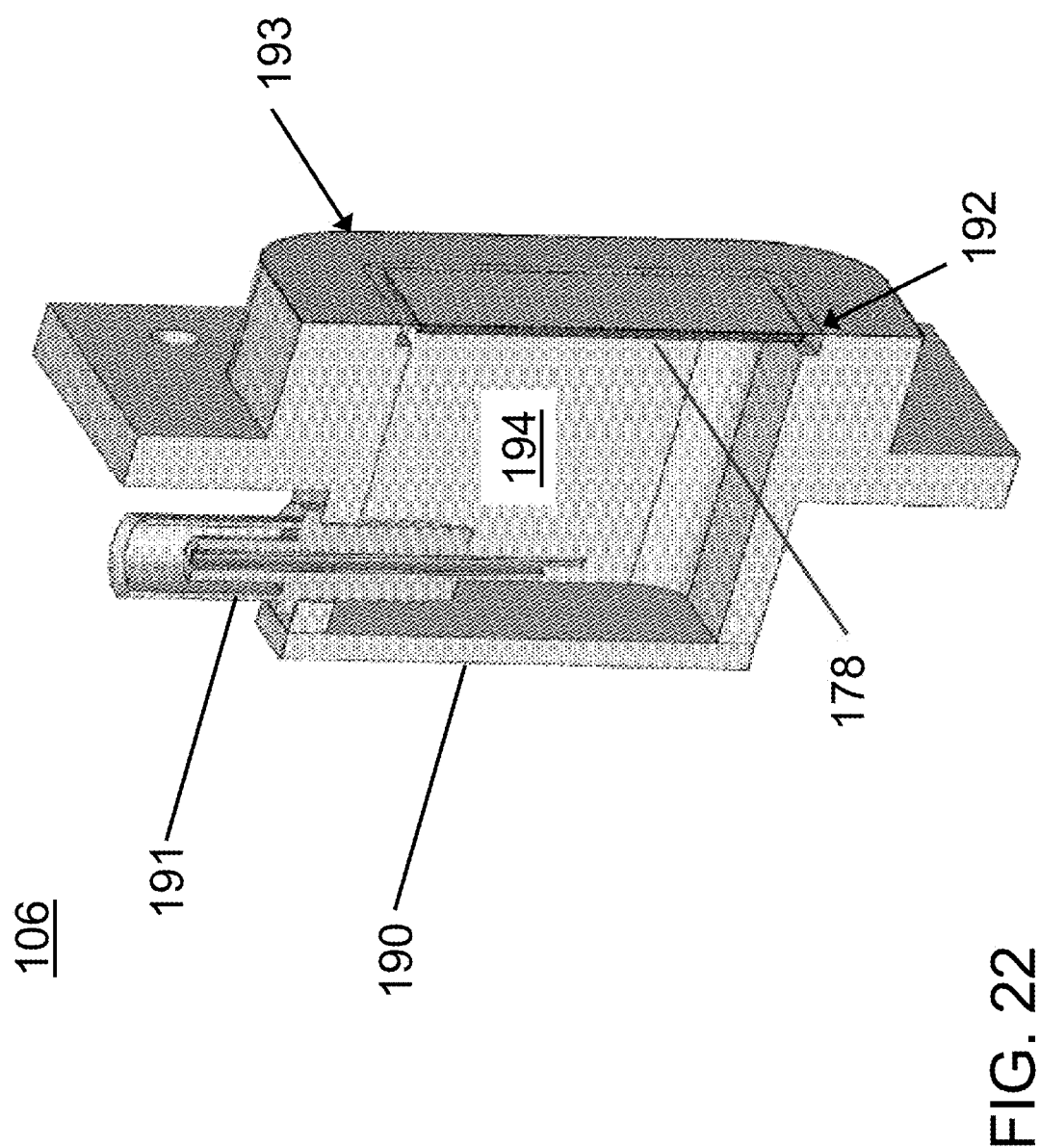
FIG. 22 is a magnified cross-sectional view of the transducer assembly of the acoustophoretic device of FIG. 17.

A third exemplary embodiment of an acoustophoretic device 700 is illustrated in FIGS. 17-22. FIG. 17 is an exterior perspective view. FIG. 18 is a perspective side cross-sectional view of the device. FIG. 19 is a side cross-sectional view of the device. FIG. 20 is a front cross-sectional view of the device. FIG. 21 is a magnified perspective side cross-sectional view of the acoustic chamber. FIG. 22 is a magnified perspective side cross-sectional view of the ultrasonic transducer. This particular embodiment is also built in a modular fashion from multiple components.

Figure 10:
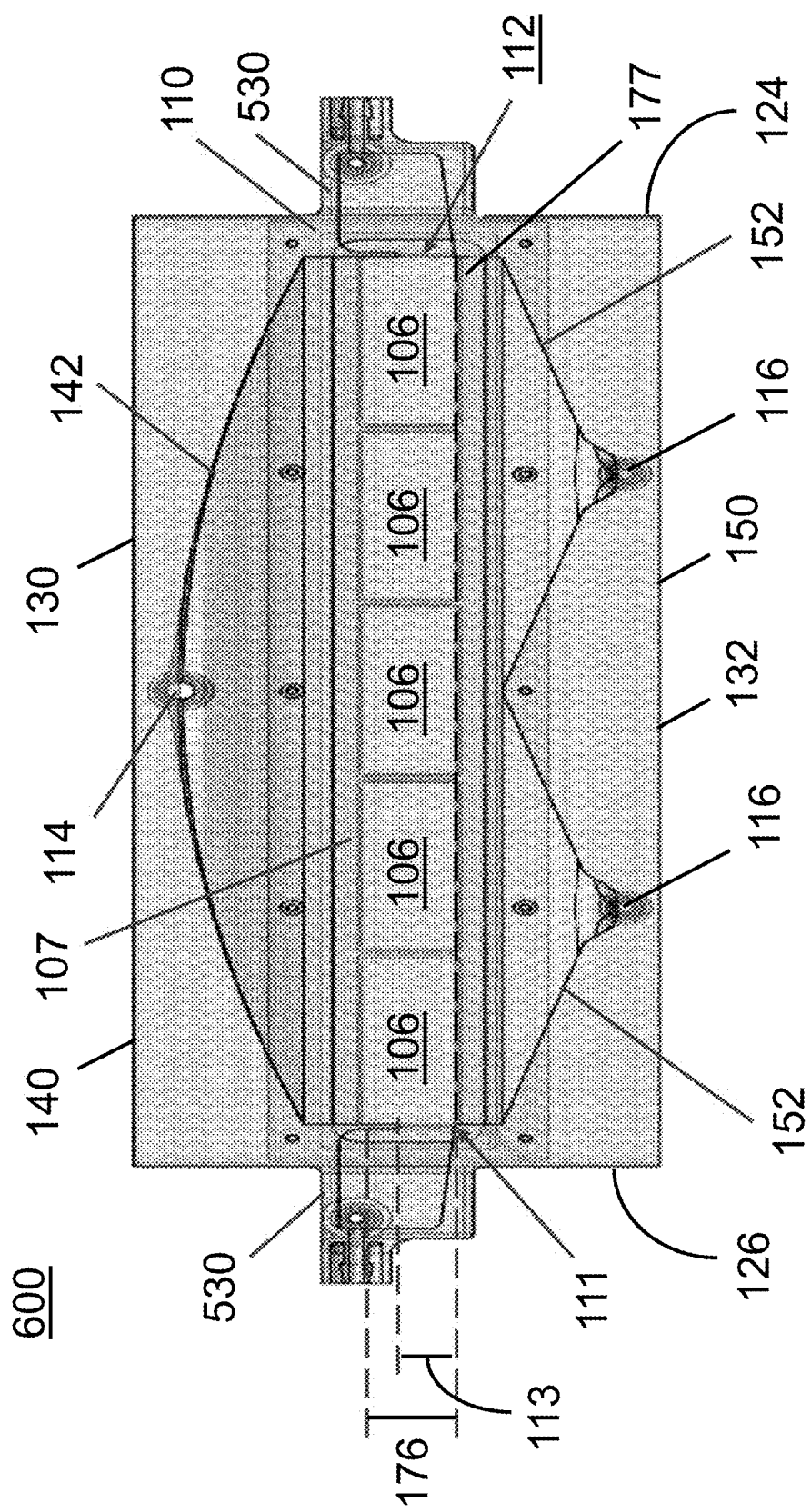
FIG. 10 is a front cross-sectional view of a second exemplary acoustophoretic device according to the present disclosure. The device also has an acoustic chamber whose horizontal cross-sectional area is greater than its vertical cross-sectional area.
Figure 11:
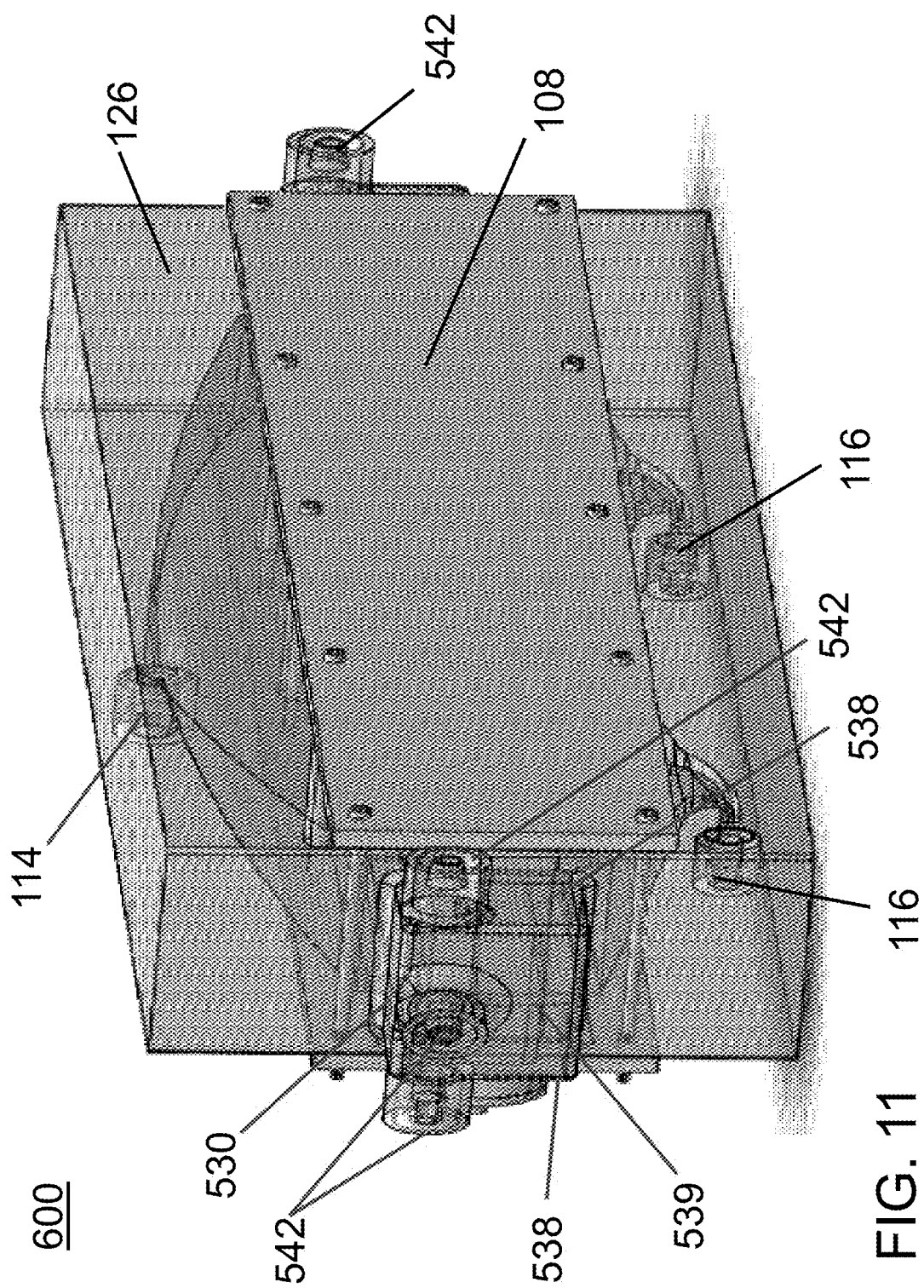
FIG. 11 is a front exterior perspective view of the device of FIG. 10.
Figure 12:
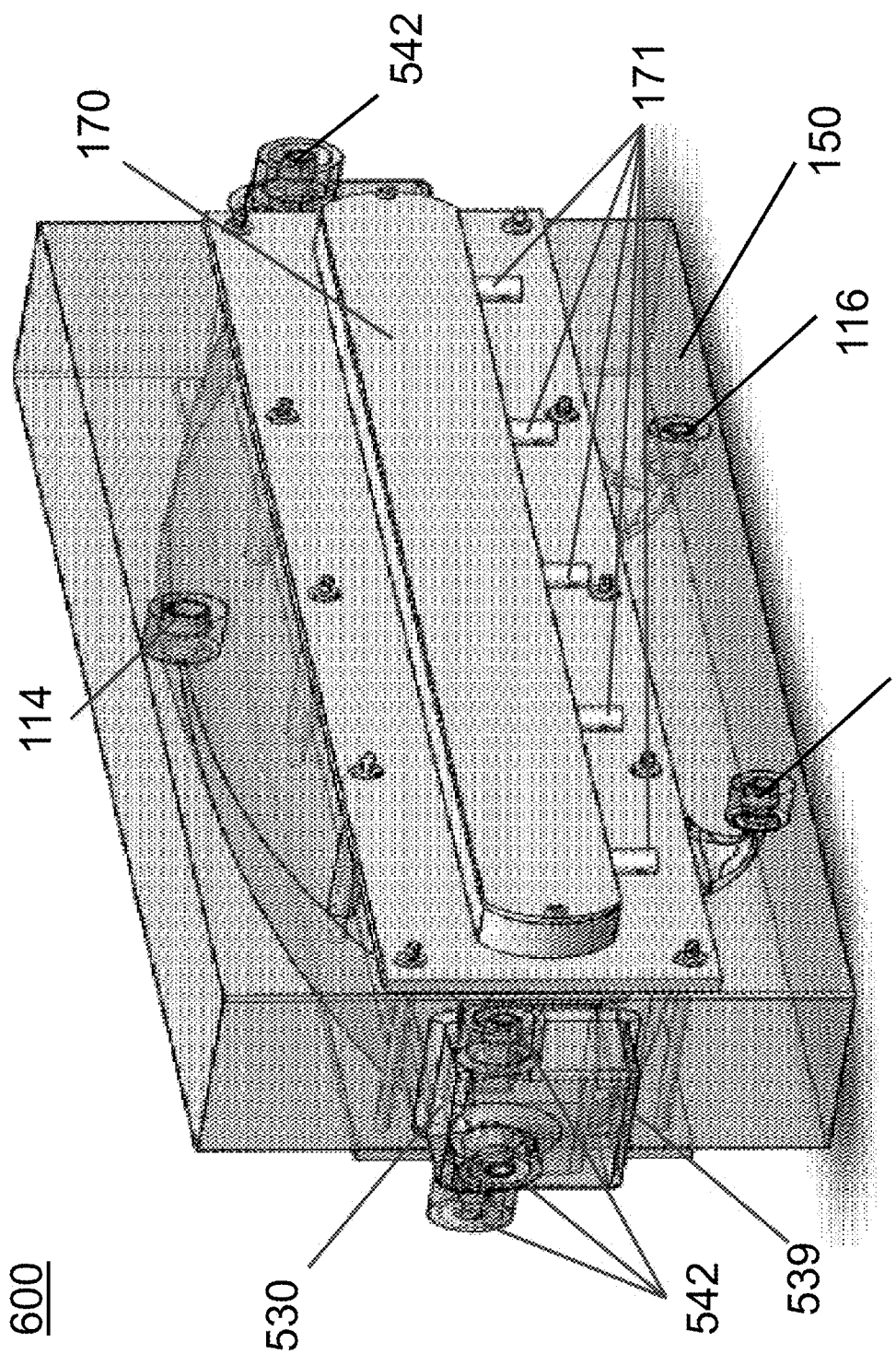
FIG. 12 is a rear exterior perspective view of the device of FIG. 10.
Figure 13:
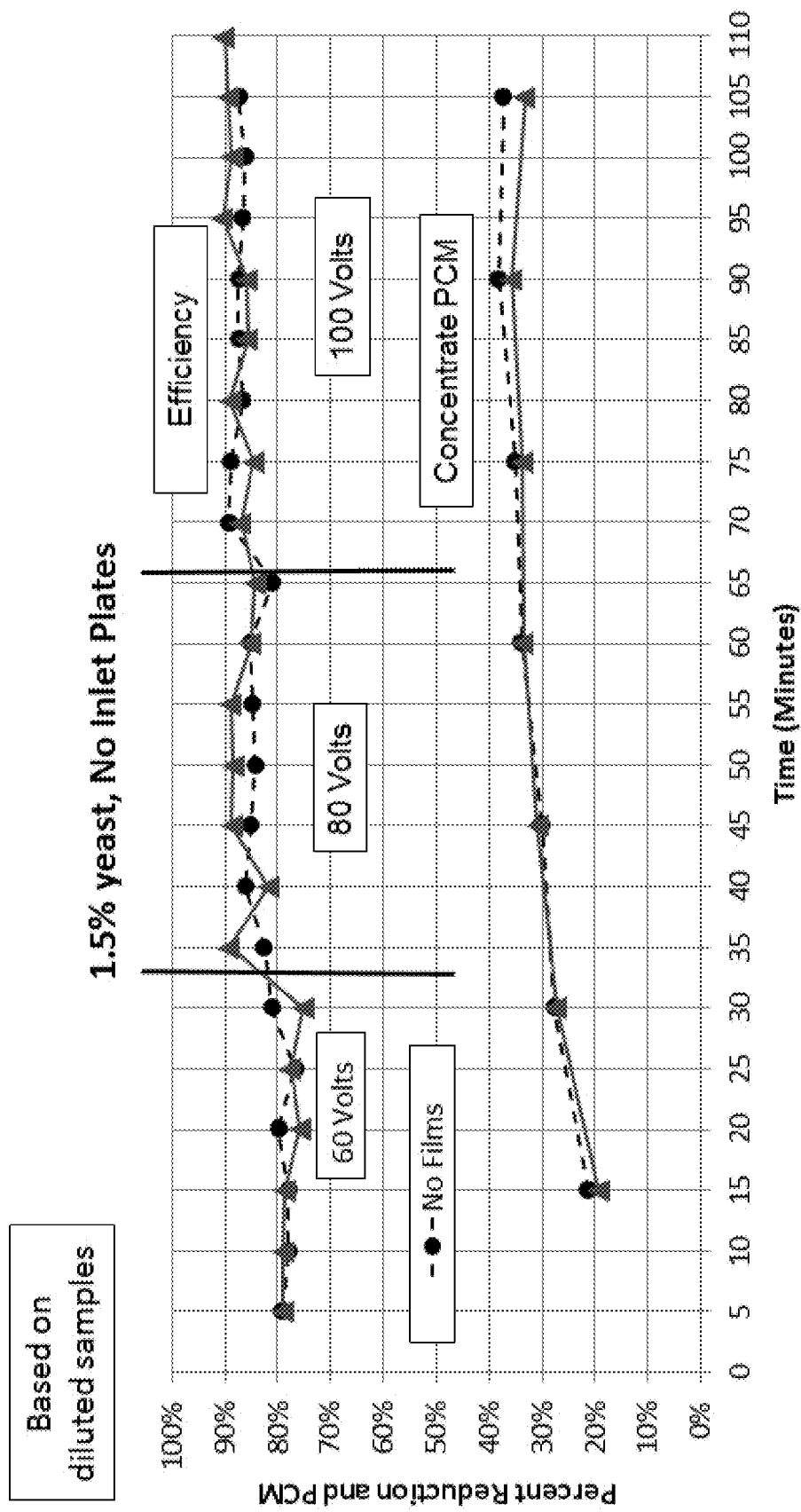
FIG. 13 is a graph showing the percent reduction/clarification (upper lines) and phase contrast microscopy (lower lines) over time of a 1.5% yeast mixture flowed at 810 mL/minute through a 9 inch by 3 inch by 2 inch (length by width by height) acoustophoretic device according to the present disclosure having no dump diffuser and operated at 60 volts, 80 volts, and 100 volts. The lighter lines with circular points represent device using films, while the darker lines with square points represent devices not using films.
Figure 14:
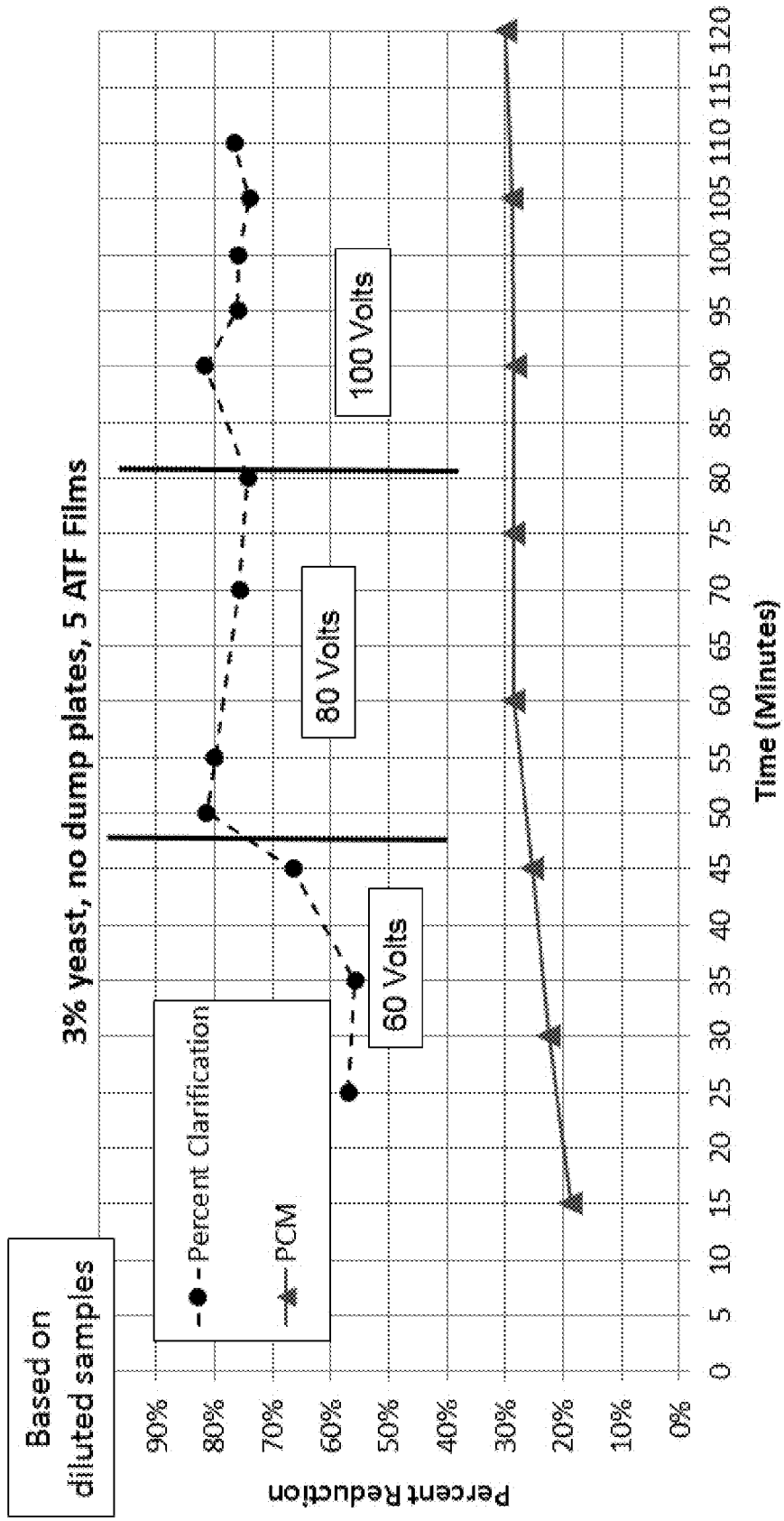
FIG. 14 is a graph showing the percent reduction/clarification (upper lines) and phase contrast microscopy (lower lines) over time of a 3% yeast mixture flowed at 810 mL/minute through a 9 inch by 3 inch by 2 inch (length by width by height) acoustophoretic device according to the present disclosure having no dump diffuser, five alternating tangential flow (ATF) films, and operated at 60 volts, 80 volts, and 100 volts.

Starting with FIG. 17, the acoustophoretic device 700 shares some similarities with the devices illustrated in FIG. 1 and FIG. 10. Device 700 has a first side end 122 and a second opposite side end 124. A sidewall 110, roof 140 and a base 150 are present to define the interior volume 107. A dump diffuser 530 is present on each side end 122, 124, which acts as the fluid inlet 112 to the interior volume 107 of the device. The dump diffuser here has three inlet flow ports 542, like that described in the device of FIG. 10. The roof 140 includes a conical interior surface 142 that leads to the fluid outlet 114 at the top end 130. A concentrate outlet 116 is present in the base 150, with a conical surface leading to the concentrate outlet at the bottom end 132. An ultrasonic transducer 106 is present on the rear side, and a reflector 108 is present on the front side opposite the transducer.

Referring now to FIG. 18, it can be seen that the fluid outlet 114 and the concentrate outlets 116 lead from the top/bottom ends of the interior volume 107 to one of the side ends 124 of the device, i.e. a common side where a fluid inlet 112 is present. As previously explained above, the fluid outlet 112 generally allows for recovery of clarified fluid from the interior volume 107. The concentrate outlet 116 generally allows for recovery or collection of particles, cells.

Referring now to FIG. 19, the interior surface 142 of the roof 140 leading to the fluid outlet 114 can be seen, as can the angled walls 152 leading to the concentrate outlet 116. The bottom of the acoustic chamber is indicated with dotted line 121, and the top of the acoustic chamber is indicated with dotted line 119. The interior surface 142 has an interior angle B measured relative to dotted line 119, with the angle B being in embodiments from about 11° to about 60°, including about 30° to about 45°. Similarly, the angled walls 152 have an angle A measured relative to dotted line 121, with the angle A being in embodiments from about 11° to about 60°, including about 30° to about 45°. O-rings 180 can be disposed between the roof/base and the acoustic chamber so as to provide a fluid-tight seal therebetween.

Referring now to FIG. 20, it is again seen that the fluid outlet 114 and the concentrate outlets 116 lead from the top/bottom ends of the interior volume 107 to one of the side ends 124 of the device, i.e. a common side where a fluid inlet 112 is present.

The piezoelectric material 178 of the ultrasonic transducer is seen, as is the fluid inlet 112 into the acoustic chamber 107 from the dump diffuser 530. The hollow chamber 540 is also seen. The piezoelectric material 178 has a height 176. The fluid inlet 112 also has a height 113. The height 113 of the fluid inlet 112 is about 60% of the height 176 of the piezoelectric material 178. In embodiments, the height of the fluid inlet can be from about 5% to about 75% of the height of the piezoelectric material. Again, a bottom edge 111 of the fluid inlet 112 is aligned with a bottom edge 177 of the piezoelectric material.

Turning now to FIG. 21, a magnified view of the acoustic chamber 107 of the device 700 can be seen, which is sandwiched between the ultrasonic transducer 106 and the reflector 108. A very small gap (e.g., 0.010 inches) is present between the fluid inlet 112 and the transducer 106. This gap can be filled with, for example, an O-ring, as depicted in FIG. 19. There is also a very short gap (e.g., <0.025 inch) between the bottom edge 177 of the piezoelectric material of the transducer and the angled walls 152 of the base.

FIG. 22 provides a magnified cross-sectional view of the ultrasonic transducer 106. As shown in FIG. 18 and FIG. 19, the ultrasonic transducer 106 is generally located in the sidewall of the device. As depicted here, the ultrasonic transducer includes a housing 190. An air gap 194 is present within the housing of the transducer. A connector 191 is present and spaced apart from the piezoelectric material 178, which is in the form of a crystal. A potting material 192, such as epoxy, is used to attach the piezoelectric material 178 to the housing. An adhesive-backed film 193, made for example from a polyetheretherketone (PEEK), is then attached to the exterior surface of the piezoelectric material 178 and the housing. This film can act as a wear layer. The wear layer generally has a thickness of a half wavelength or less (e.g., 0.050 inches). Additional features of the ultrasonic transducer(s) used in the present devices will be explained in greater detail herein.

One specific application for the acoustophoresis devices disclosed herein is in the processing of bioreactor materials. The fluid stream entering these devices is a mixture of a host/primary fluid (e.g. water, cell culture media) and a secondary particulate. The secondary particulate can include cells and expressed materials such as biomolecules (e.g. recombinant proteins or monoclonal antibodies or viruses). The devices can be used to concentrate larger particles, such as cells, from the mixture, so that there are two different streams exiting the device. First, a stream of concentrated cells and some fluid can exit through the concentrate outlet. Second, a stream of clarified fluid containing expressed materials such as biomolecules can exit through the fluid outlet. Depending on what material is desired to be recovered, either of these two streams exiting the device can be recycled to the bioreactor.

The acoustophoresis devices of the present disclosure, which use three-dimensional acoustic standing waves, may also be coupled with a standard filtration process upstream or downstream, such as depth filtration using diatomaceous earth, tangential flow filtration (TFF), or other physical filtration processes, as desired.

Desirably, flow rates through the devices of the present disclosure can be a minimum of 1 mL/min, or a minimum of about 800 mL/min, and desirably even higher flow rates can be achieved. In alternate units, these flow rates may be about 0.005 mL/min per $cm^2$ of cross-sectional area of the acoustic chamber, or about 4.5 mL/min/$cm^2$. This is true for batch reactors, fed-batch bioreactors and perfusion bioreactors.

It may be helpful to provide an explanation now of how multi-dimensional acoustic standing waves (particularly three-dimensional acoustic standing waves) are generated. The multi-dimensional acoustic standing wave needed for particle collection is obtained by driving an ultrasonic transducer at a frequency that both generates the acoustic standing wave and excites a fundamental 3D vibration mode of the transducer crystal. Perturbation of the piezoelectric crystal in an ultrasonic transducer in a multimode fashion allows for generation of a multidimensional acoustic standing wave. A piezoelectric crystal can be specifically designed to deform in a multimode fashion at designed frequencies, allowing for generation of a multi-dimensional acoustic standing wave. The multi-dimensional acoustic standing wave may be generated by distinct modes of the piezoelectric crystal such as a 3×3 mode that would generate multidimensional acoustic standing waves. A multitude of multidimensional acoustic standing waves may also be generated by allowing the piezoelectric crystal to vibrate through many different mode shapes. Thus, the crystal would excite multiple modes such as a 0×0 mode (i.e. a piston mode) to a 1×1, 2×2, 1×3, 3×1, 3×3, and other higher order modes and then cycle back through the lower modes of the crystal (not necessarily in straight order). This switching or dithering of the crystal between modes allows for various multidimensional wave shapes, along with a single piston mode shape to be generated over a designated time.

Some further explanation of the ultrasonic transducers used in the devices, systems, and methods of the present disclosure may be helpful as well. In this regard, the transducers use a piezoelectric crystal, usually made of PZT-8 (lead zirconate titanate). Such crystals may have a 1 inch diameter and a nominal 2 MHz resonance frequency, and may also be of a larger size. Each ultrasonic transducer module can have only one crystal, or can have multiple crystals that each act as a separate ultrasonic transducer and are either controlled by one or multiple amplifiers. The crystals can be square, rectangular, irregular polygon, or generally of any arbitrary shape. The transducer(s) is/are used to create a pressure field that generates forces of the same order of magnitude both orthogonal to the standing wave direction (lateral) and in the standing wave direction (axial).

Figure 23:
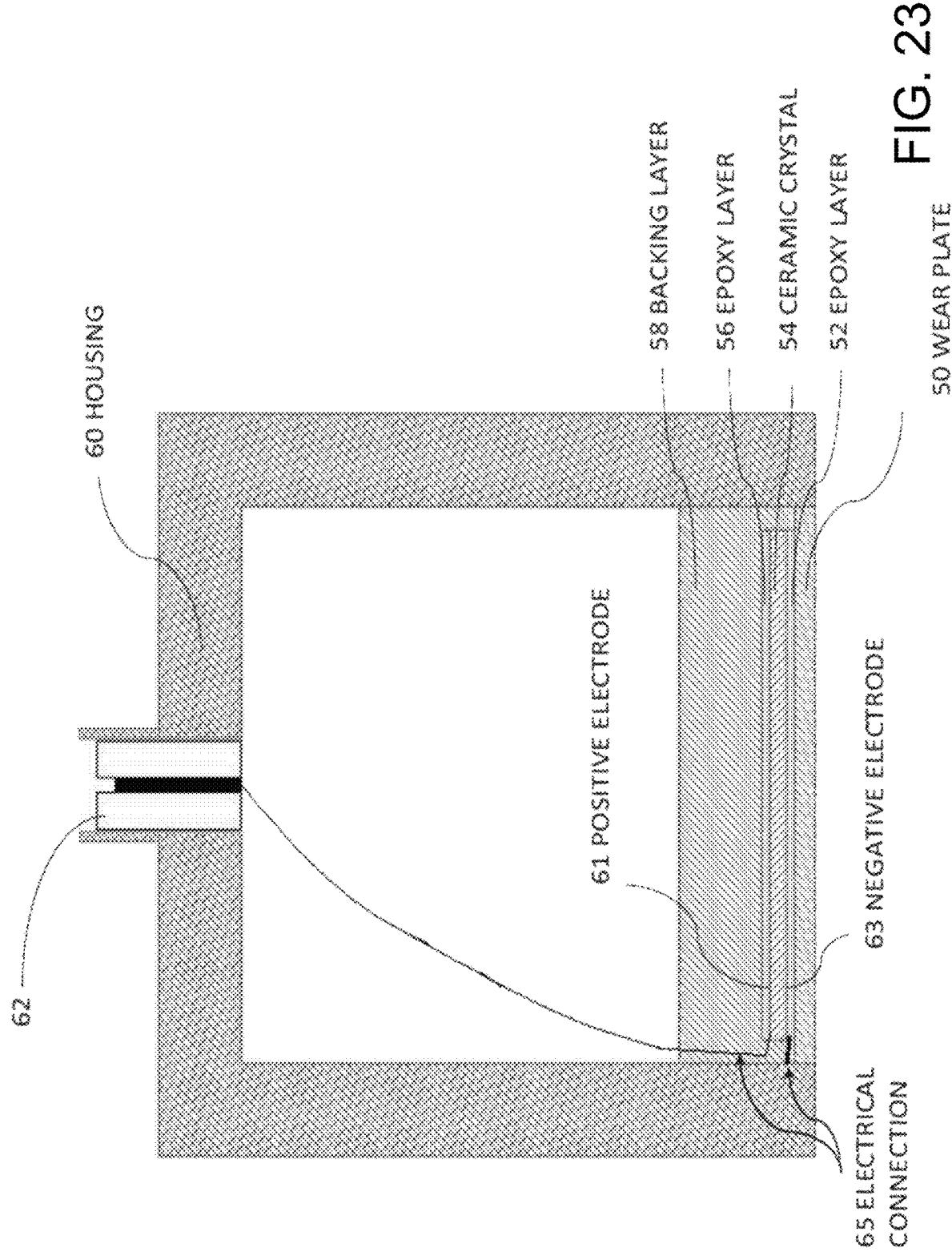
FIG. 23 is a cross-sectional diagram of a conventional ultrasonic transducer.
Figure 25:
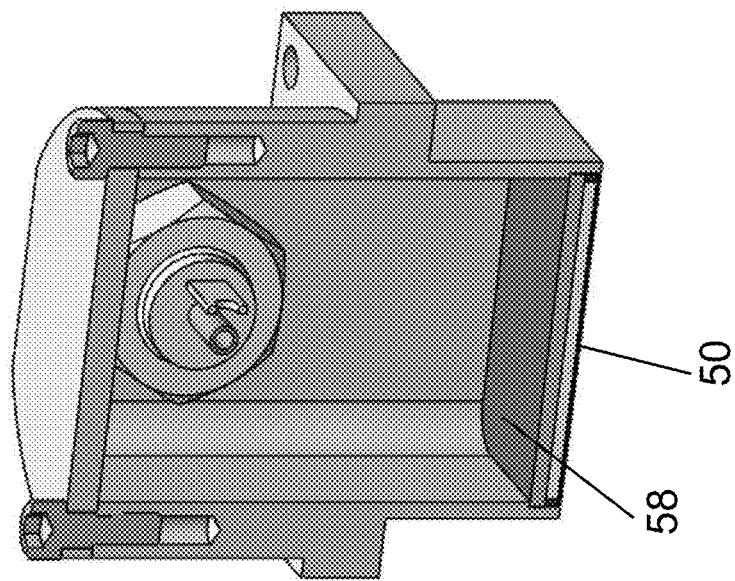
FIG. 25 is a cross-sectional diagram of an ultrasonic transducer of the present disclosure. An air gap is present within the transducer, and a backing layer and wear plate are present.

FIG. 23 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 24:
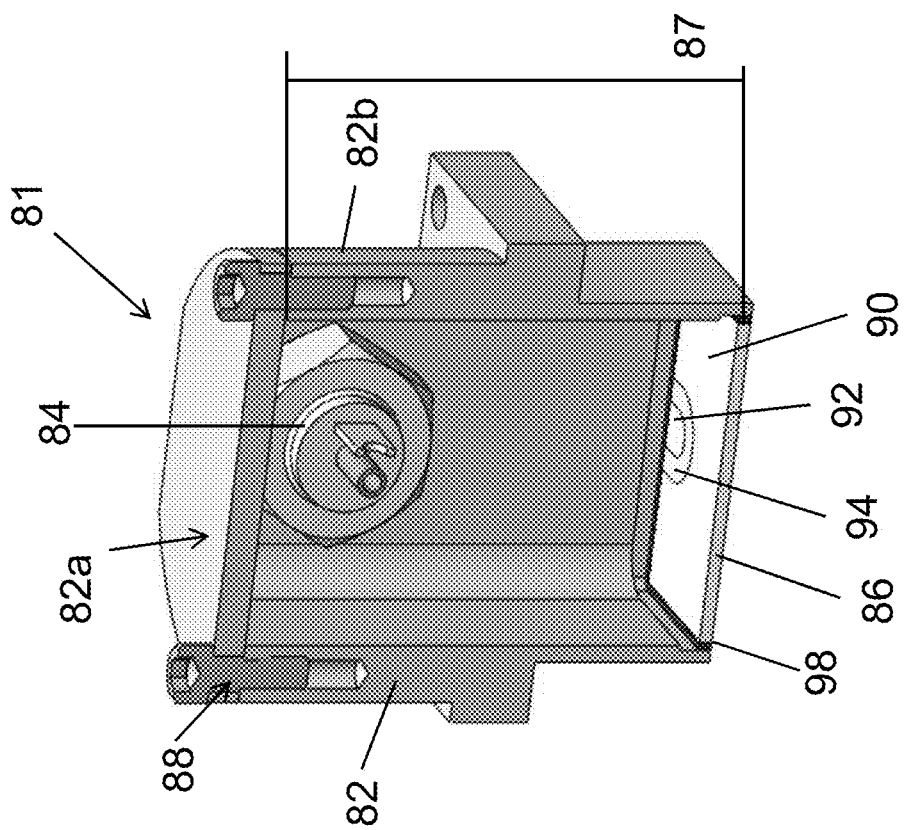
FIG. 24 is a cross-sectional diagram of an ultrasonic transducer of the present disclosure. An air gap is present within the transducer, and no backing layer or wear plate is present.

FIG. 24 is a cross-sectional view of an ultrasonic transducer 81 of the present disclosure. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and $O_2^-$ ions. As an example, a PZT (lead zirconate titanate) crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 5.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes (i.e. near eigenfrequency) with a high Q-factor. The vibrating ceramic crystal/disk is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer comprising a crystal with a backing, the crystal vibrates with a more uniform displacement, like a piston. Removing the backing allows the crystal to vibrate in a non-uniform displacement mode. The higher order the mode shape of the crystal, the more nodal lines the crystal may have. The higher order modal displacement of the crystal creates more trapping lines, although the correlation of trapping line to node is not necessarily one to one, and driving the crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymers or polymer films. Organic and biocompatible coatings such as silicone or polyurethane are also usable as a wear surface.

Figure 26:
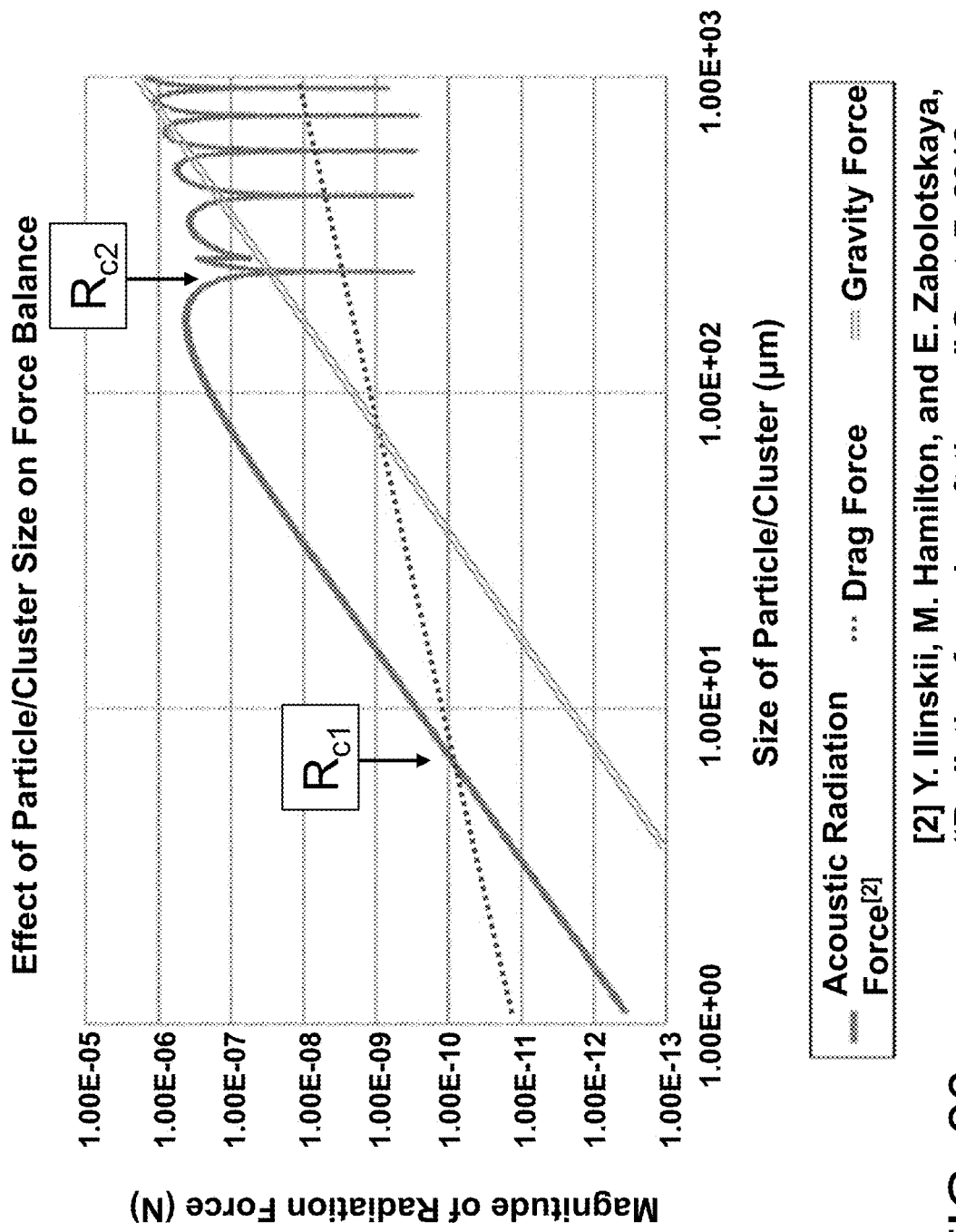
FIG. 26 is a graph showing the relationship of the acoustic radiation force, gravity/buoyancy force, and Stokes' drag force to particle size. The horizontal axis is in microns (μm) and the vertical axis is in Newtons (N).

FIG. 26 is a log-log graph (logarithmic y-axis, logarithmic x-axis) that shows the scaling of the acoustic radiation force, fluid drag force, and buoyancy force with particle radius, and provides an explanation for the separation of particles using acoustic radiation forces. The buoyancy force is a particle volume dependent force, and is therefore negligible for particle sizes on the order of micron, but grows, and becomes significant for particle sizes on the order of hundreds of microns. The fluid drag force (Stokes drag force) scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 26, this happens at a particle size labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As particles cluster, the total drag on the cluster is much lower than the sum of the drag forces on the individual particles. In essence, as the particles cluster, they shield each other from the fluid flow and reduce the overall drag of the cluster. As the particle cluster size grows, the acoustic radiation force reflects off the cluster, such that the net acoustic radiation force decreases per unit volume. The acoustic lateral forces on the particles may be different from the drag forces for the clusters to remain stationary and grow in size. For example, the acoustic lateral forces may be larger than the drag forces to permit particles to be trapped, cluster and grow in size.

Particle size growth continues until the buoyancy force becomes dominant, which is indicated by a second critical particle size, $R_{c2}$. The buoyancy force per unit volume of the cluster remains constant with cluster size, since it is a function of the particle density, cluster concentration and gravity constant. Therefore, as the cluster size increases, the buoyancy force on the cluster increases faster than the acoustic radiation force. At the size $R_{c2}$, the particles will rise or sink, depending on their relative density with respect to the host fluid. At this size, acoustic forces are secondary, gravity/buoyancy forces become dominant, and the particles naturally drop out or rise out of the host fluid. Not all particles will drop out, and those remaining particles and new particles entering the acoustic chamber will continue to move to the three-dimensional nodal locations, repeating the growth and drop-out process. This phenomenon explains the quick drops and rises in the acoustic radiation force beyond size $R_{c2}$. Thus, FIG. 6 explains how small particles can be trapped continuously in a standing wave, grow into larger particles or clumps, and then eventually will rise or settle out because of increased buoyancy force.

The size, shape, and thickness of the transducer determine the transducer displacement at different frequencies of excitation, which in turn affects particle separation efficiency. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 27:
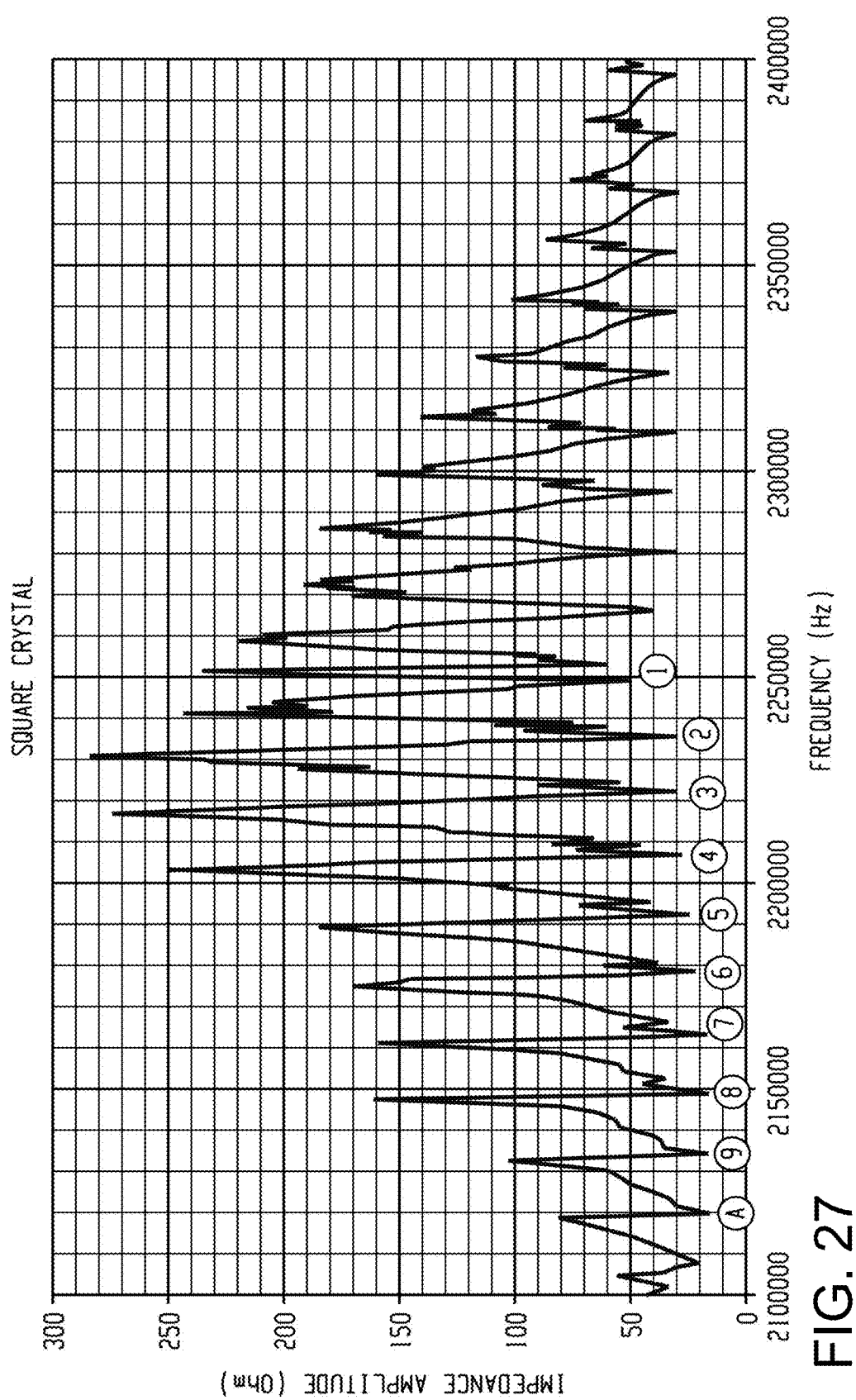
FIG. 27 is a graph of electrical impedance amplitude versus frequency for a square transducer driven at different frequencies.

FIG. 27 shows the measured electrical impedance amplitude of the transducer as a function of frequency in the vicinity of the 2.2 MHz transducer resonance. The minima in the transducer electrical impedance correspond to acoustic resonances of a water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. Higher order transducer displacement patterns result in higher trapping forces and multiple stable trapping lines for the captured particles.

To investigate the effect of the transducer displacement profile on acoustic trapping force and particle separation efficiencies, an experiment was repeated ten times, with all conditions identical except for the excitation frequency. Ten consecutive acoustic resonance frequencies, indicated by circled numbers 1-9 and letter A on FIG. 27, were used as excitation frequencies. The conditions were experiment duration of 30 min, a 1000 ppm oil concentration of approximately 5-micron SAE-30 oil droplets, a flow rate of 500 ml/min, and an applied power of 20 W.

As the emulsion passed by the transducer, the trapping lines of oil droplets were observed and characterized. The characterization involved the observation and pattern of the number of trapping lines across the fluid channel, as shown in FIG. 28A, for seven of the ten resonance frequencies identified in FIG. 27.

FIG. 28B shows an isometric view of the system in which the trapping line locations are being determined. FIG. 28C is a view of the system as it appears when looking down the inlet, along arrow 814. FIG. 28D is a view of the system as it appears when looking directly at the transducer face, along arrow 816.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. Different displacement profiles of the transducer can produce different (more) trapping lines in the standing waves, with more gradients in displacement profile generally creating higher trapping forces and more trapping lines. It is noted that although the different trapping line profiles shown in FIG. 28A were obtained at the frequencies shown in FIG. 27, these trapping line profiles can also be obtained at different frequencies.

FIG. 28A shows the different crystal vibration modes possible by driving the crystal to vibrate at different fundamental frequencies of vibration. The 3D mode of vibration of the crystal is carried by the acoustic standing wave across the fluid in the chamber all the way to the reflector and back. The resulting multi-dimensional standing wave can be thought of as containing two components. The first component is a planar out-of-plane motion component (uniform displacement across crystal surface) of the crystal that generates a standing wave, and the second component is a displacement amplitude variation with peaks and valleys occurring in both lateral directions of the crystal surface. Three-dimensional force gradients are generated by the standing wave. These three-dimensional force gradients result in lateral radiation forces that stop and trap the particles with respect to the flow by overcoming the viscous drag force. In addition, the lateral radiation forces are responsible for creating tightly packed clusters of particles. Therefore, particle separation and gravity-driven collection depends on generating a multi-dimensional standing wave that can overcome the particle drag force as the mixture flows through the acoustic standing wave. Multiple particle clusters are formed along trapping lines in the axial direction of the standing wave, as presented schematically in FIG. 28A.

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. A method for separating a secondary fluid or particulate from a mixture with a host fluid, comprising:
   placing the mixture in an acoustophoretic device that comprises:
   an acoustic chamber;
   at least one ultrasonic transducer coupled to the acoustic chamber and configured to generate a multi-dimensional acoustic standing wave in the acoustic chamber;
   a reflector across the acoustic chamber from the at least one ultrasonic transducer; and
   an interior volume of at least 40 cubic inches;
   exciting the at least one transducer in a higher order mode to generate the multi-dimensional acoustic standing wave in the acoustic chamber; and
   trapping the secondary fluid or particulate via the acoustic standing wave such that the secondary fluid or particulate agglomerates, aggregates, clusters, or coalesces together and separates from the host fluid.

2. The method of claim 1, further comprising flowing the mixture through the acoustophoretic device.

3. The method of claim 2, further comprising flowing the mixture through a dump diffuser into the acoustic chamber.

4. The method of claim 2, further comprising flowing the mixture in a flow direction normal to an axial direction of the acoustic standing wave generated by the at least one ultrasonic transducer.

5. The method of claim 2, further comprising flowing the mixture into the acoustic chamber via at least two inlets arranged at opposite ends of the acoustic chamber.

6. The method of claim 1, wherein the at least one transducer further comprises a plurality of transducers spanning the length of the acoustic chamber.

7. The acoustophoretic device of claim 6, wherein the plurality of transducers includes a first row with at least two transducers located above a second row with at least two transducers.

8. The method of claim 1, wherein the multi-dimensional acoustic standing wave includes an axial force component and a lateral force component which are of the same order of magnitude.

9. The method of claim 1, further comprising generating the acoustic standing wave in the acoustic chamber through an acoustically transparent film.

10. A method for separating a secondary fluid or particulate from a mixture with a primary fluid, comprising:
    flowing the mixture of the primary fluid and the secondary fluid or particulate at a rate of at least 25 mL/min through an acoustophoretic device that comprises:
    an acoustic chamber;
    at least one ultrasonic transducer coupled to the acoustic chamber and configured to generate a multi-dimensional acoustic standing wave in the acoustic chamber; and
    a reflector across the acoustic chamber from the at least one ultrasonic transducer;
    exciting the at least one transducer in a higher order mode to generate the multi-dimensional acoustic standing wave in the acoustic chamber; and
    trapping the secondary fluid or particulate via the acoustic standing wave such that the secondary fluid or particulate agglomerates, aggregates, clusters or coalesces together and separates from the primary fluid.

11. The method according to claim 10, further comprising flowing the mixture into the acoustic chamber at a location between about 5% and about 25% of the height of the acoustic chamber.

12. The method according to claim 10, further comprising flowing the mixture into the acoustic chamber at a rate of at least 800 mL/min.

13. The method according to claim 10, further comprising flowing the mixture into the acoustic chamber at a rate in the range of from about 0.005 mL/min/cm2 to about 4.5 mL/min/cm2.

14. The method according to claim 10, further comprising flowing the mixture in a flow direction normal to an axial direction of the acoustic standing wave generated by the at least one ultrasonic transducer.

15. The method according to claim 10, wherein the wave is multi-dimensional acoustic standing wave that includes an axial force component and a lateral force component which are of the same order of magnitude.

16. A method for separating a secondary fluid or particulate from a mixture with a primary fluid, comprising:
   flowing the mixture of the primary fluid and the secondary fluid or particulate through an acoustophoretic device that comprises:
      an acoustic chamber;
      at least one ultrasonic transducer coupled to the acoustic chamber and configured to generate a multi-dimensional acoustic standing wave in the acoustic chamber; and
      a reflector across the acoustic chamber from the at least one ultrasonic transducer;
   exciting the at least one transducer in a higher order mode to generate the multi-dimensional acoustic standing wave in the acoustic chamber through an acoustically transparent film; and
   trapping the secondary fluid or particulate via the acoustic standing wave such that the secondary fluid or particulate agglomerates, aggregates, clusters or coalesces together and separates from the primary fluid.

* * * * *